(12) United States Patent
Zuleba

(10) Patent No.: US 7,668,820 B2
(45) Date of Patent: Feb. 23, 2010

(54) METHOD FOR LINKING DE-IDENTIFIED PATIENTS USING ENCRYPTED AND UNENCRYPTED DEMOGRAPHIC AND HEALTHCARE INFORMATION FROM MULTIPLE DATA SOURCES

(75) Inventor: Heather Zuleba, Lafayette Hill, PA (US)

(73) Assignee: IMS Software Services, Ltd., Wilmington, DE (US)

( * ) Notice: Subject to any disclaimer, the term of this patent is extended or adjusted under 35 U.S.C. 154(b) by 299 days.

(21) Appl. No.: 11/191,281

(22) Filed: Jul. 28, 2005

(65) Prior Publication Data

US 2006/0026156 A1    Feb. 2, 2006

Related U.S. Application Data

(60) Provisional application No. 60/591,734, filed on Jul. 28, 2004.

(51) Int. Cl.
*G06F 17/30* (2006.01)
*G06F 15/16* (2006.01)

(52) U.S. Cl. .................................. 707/5; 705/2; 705/3
(58) Field of Classification Search ...................... 707/5
See application file for complete search history.

(56) References Cited

U.S. PATENT DOCUMENTS

| | | | | |
|---|---|---|---|---|
| 5,084,828 A | 1/1992 | Kaufman et al. | ............. | 364/479 |
| 5,331,544 A | 7/1994 | Lu et al. | .................... | 364/401 |
| 5,420,786 A | 5/1995 | Felthauser et al. | .......... | 364/401 |
| 5,490,060 A | 2/1996 | Malec et al. | ................ | 364/401 |
| 5,519,607 A | 5/1996 | Tawil | ........................ | 364/401 |
| 5,666,492 A | 9/1997 | Rhodes et al. | ................ | 705/3 |
| 5,737,539 A | 4/1998 | Edelson et al. | ............. | 395/203 |
| 5,758,095 A | 5/1998 | Albaum et al. | ............. | 395/202 |
| 5,758,147 A | 5/1998 | Chen et al. | ................... | 395/606 |
| 5,781,893 A | 7/1998 | Felthauser et al. | .......... | 705/210 |
| 5,845,255 A | 12/1998 | Mayaud | ........................ | 705/3 |
| 6,061,658 A | 5/2000 | Chou et al. | .................... | 705/10 |
| 6,249,769 B1 | 6/2001 | Ruffin et al. | ................... | 705/7 |
| 6,285,983 B1 | 9/2001 | Jenkins | ........................ | 705/10 |
| 6,397,224 B1 * | 5/2002 | Zubeldia et al. | ............. | 707/102 |
| 6,732,113 B1 * | 5/2004 | Ober et al. | ................... | 707/102 |
| 2002/0073138 A1 * | 6/2002 | Gilbert et al. | ............... | 709/201 |
| 2002/0165736 A1 | 11/2002 | Tolle et al. | | |

(Continued)

OTHER PUBLICATIONS

International Search Report for PCT/US02/06268 dated Feb. 26, 2003.

*Primary Examiner*—Cam Y. Truong
*Assistant Examiner*—Dung K Chau
(74) *Attorney, Agent, or Firm*—Baker Botts L.L.P.

(57) ABSTRACT

A longitudinal database of de-identified patient healthcare transaction data records linked by longitudinal linking tags (IDs) is provided. A new healthcare transaction data record, which may include alphanumeric identification code attributes, third party attributes and/or demographic attributes, is assigned an linking ID associated with a previous healthcare transaction data record based upon successful comparison of either a designated set of identification code attributes or a designated set of demographic attributes. The longitudinal data base is assembled by a matching process in which a new data record is compared level by level with previous healthcare transaction data records through a hierarchy of a first series of matching levels each defined by a designated set of alphanumeric identification code attributes and a second series of matching levels each defined by a designated set of attributes including demographic attributes and then assigned the ID associated with a successfully matched reference data record.

9 Claims, 13 Drawing Sheets

U.S. PATENT DOCUMENTS

| | | | |
|---|---|---|---|
| 2002/0194025 A1* | 12/2002 | Notelovitz | 705/2 |
| 2003/0046114 A1* | 3/2003 | Davies et al. | 705/3 |
| 2004/0122792 A1* | 6/2004 | Salazar | 707/1 |
| 2004/0189707 A1* | 9/2004 | Moore et al. | 345/777 |
| 2004/0215981 A1* | 10/2004 | Ricciardi et al. | 713/202 |
| 2006/0004739 A1* | 1/2006 | Anthony et al. | 707/4 |

* cited by examiner

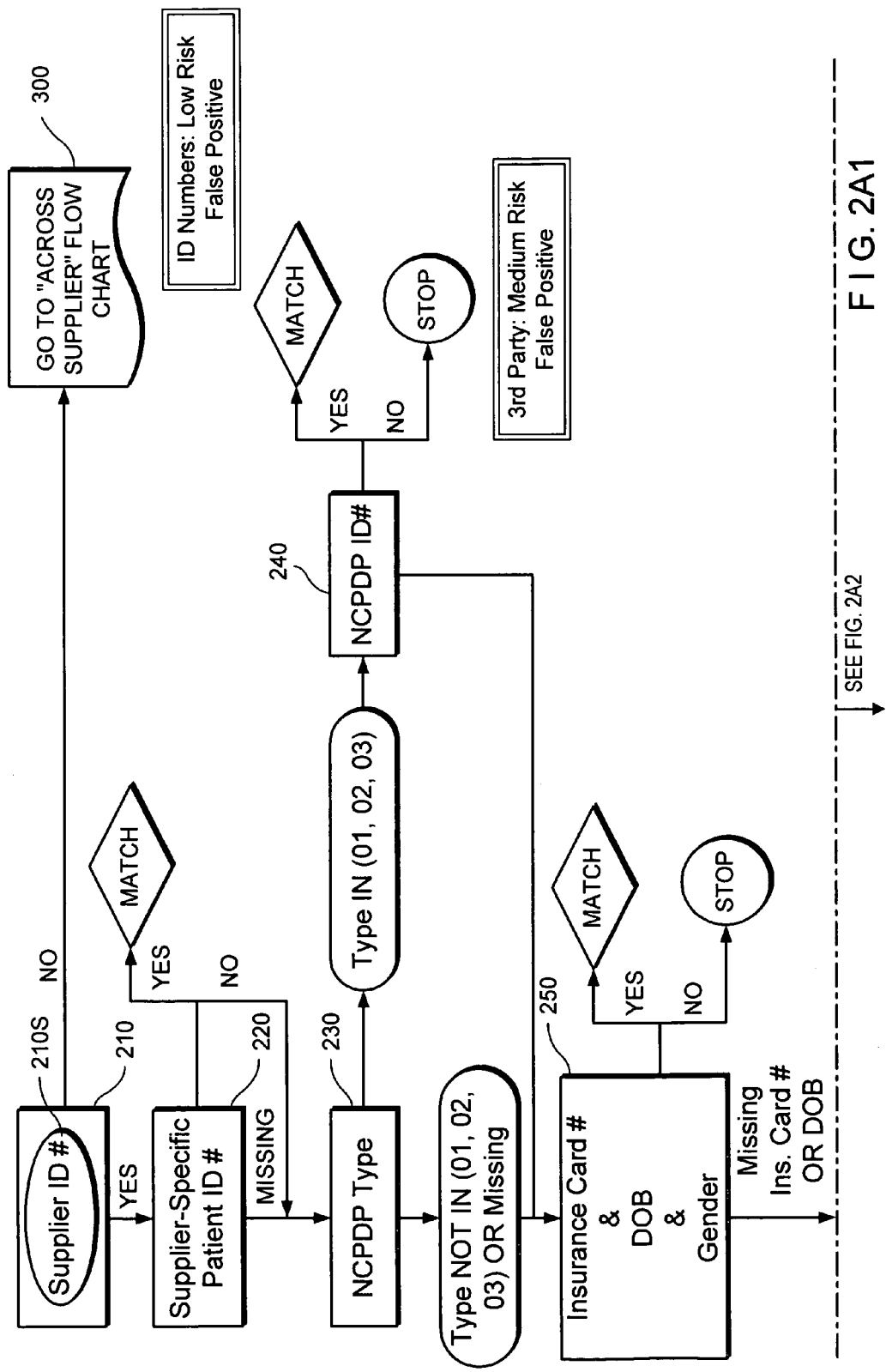
FIG. 2A1

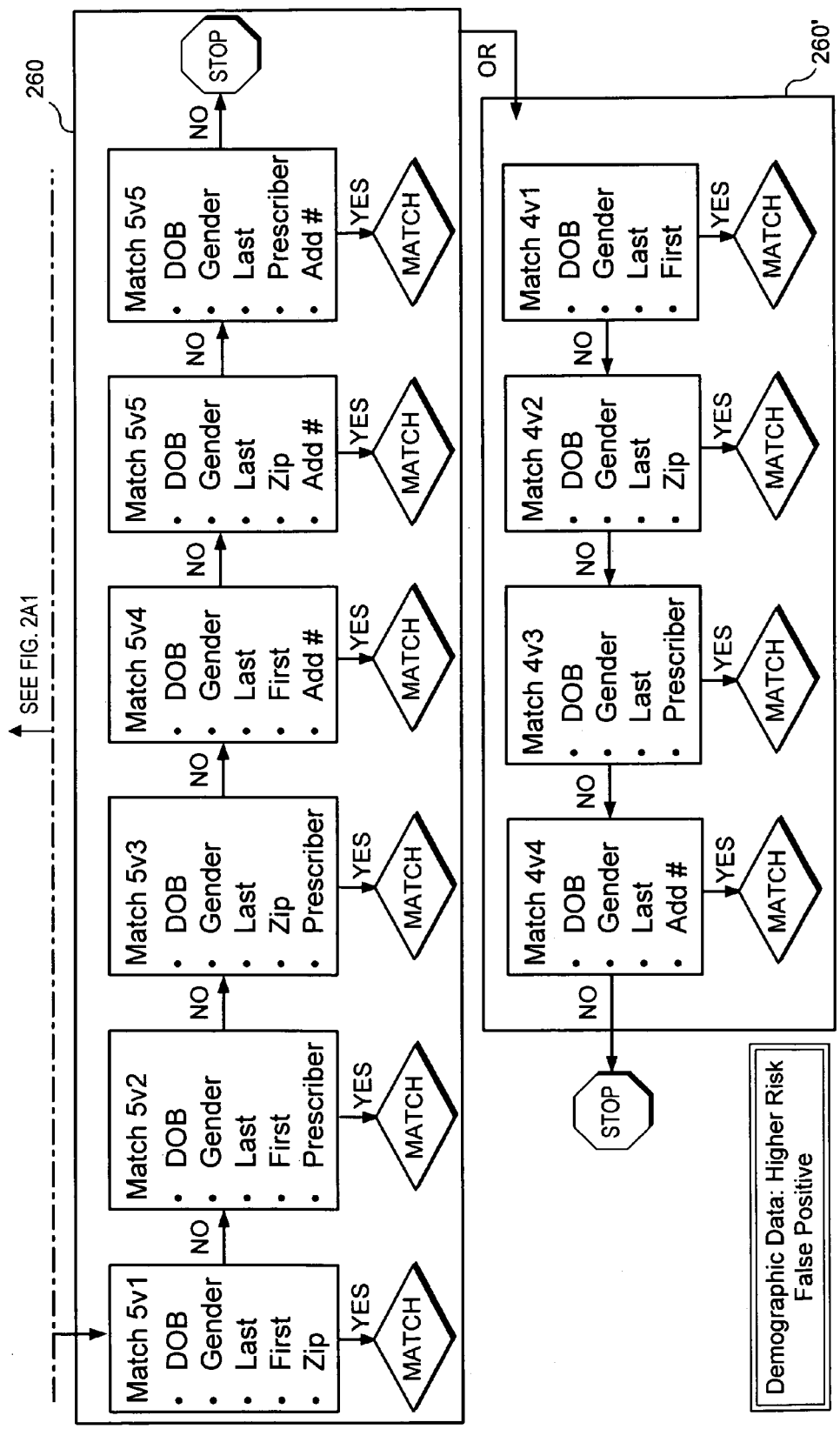
FIG. 2A2

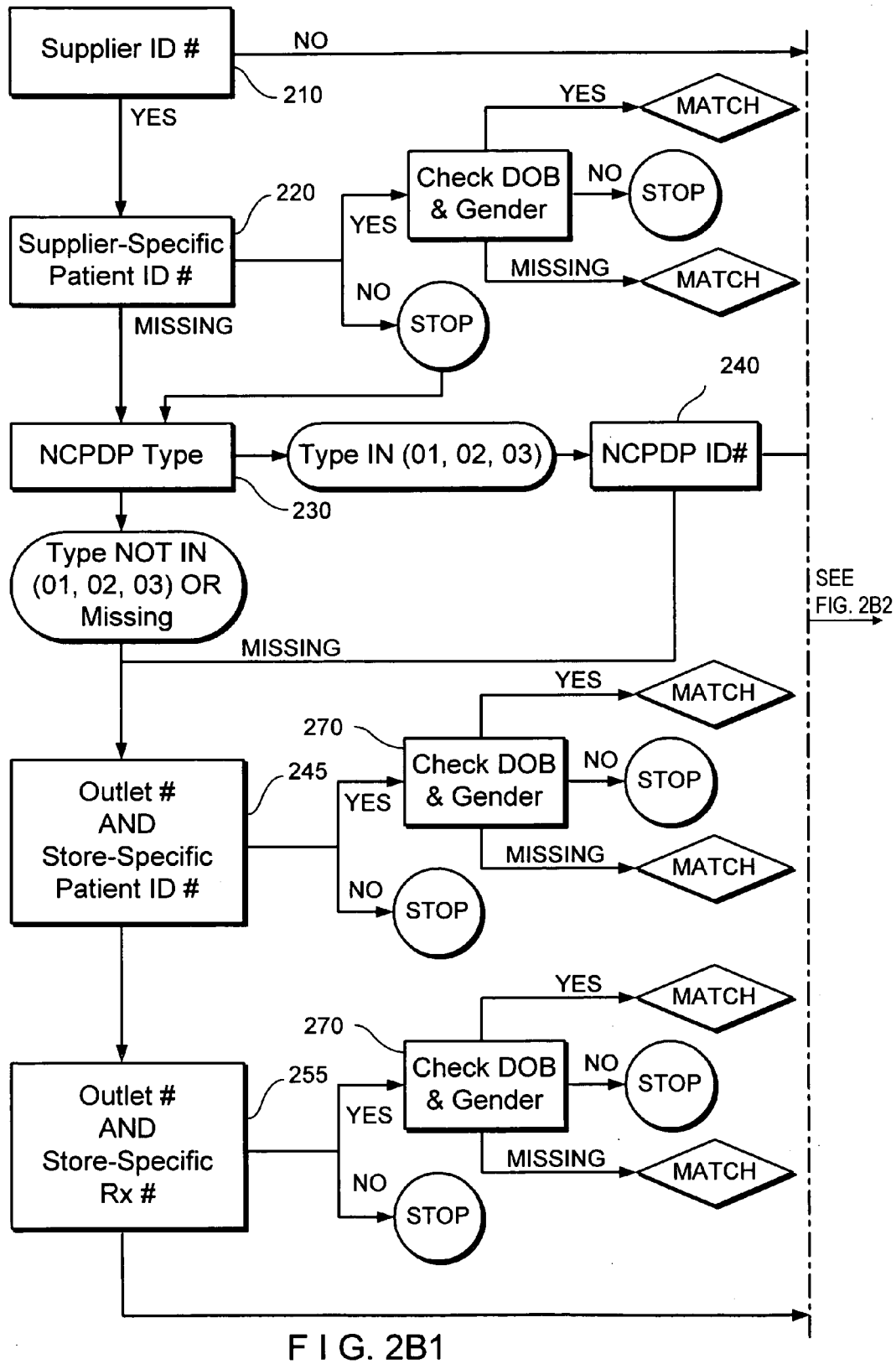
FIG. 2B1

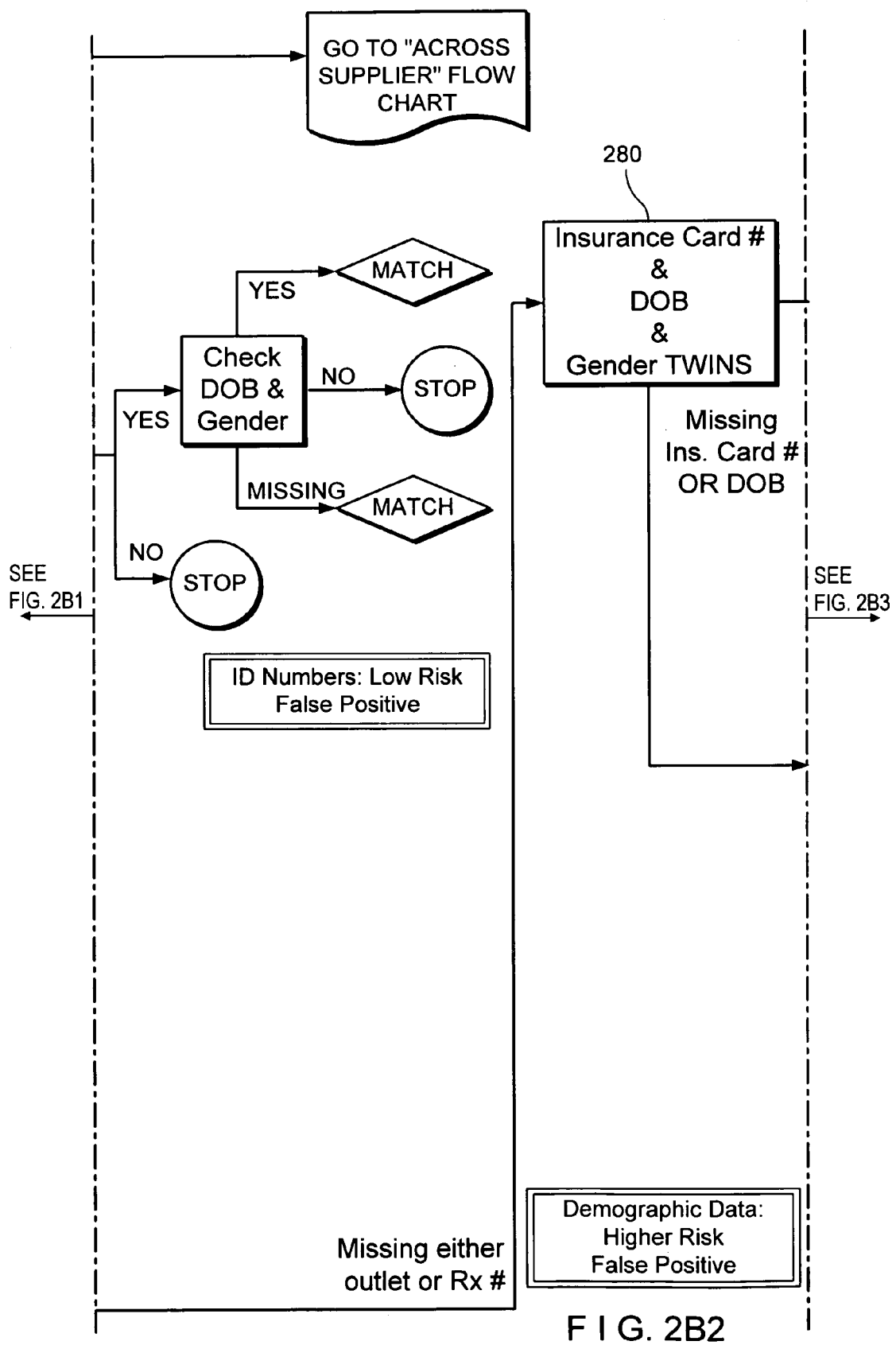
FIG. 2B2

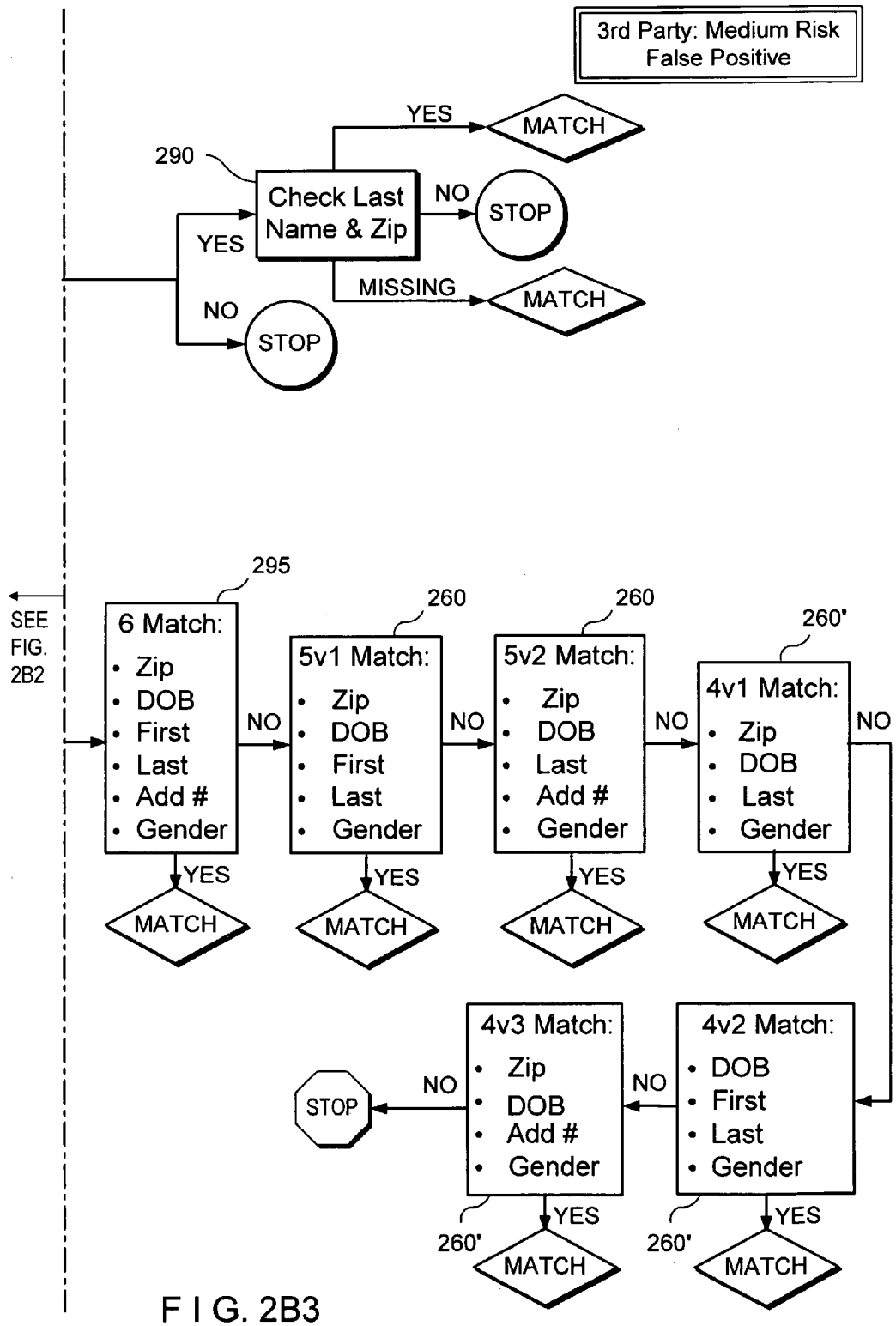
FIG. 2B3

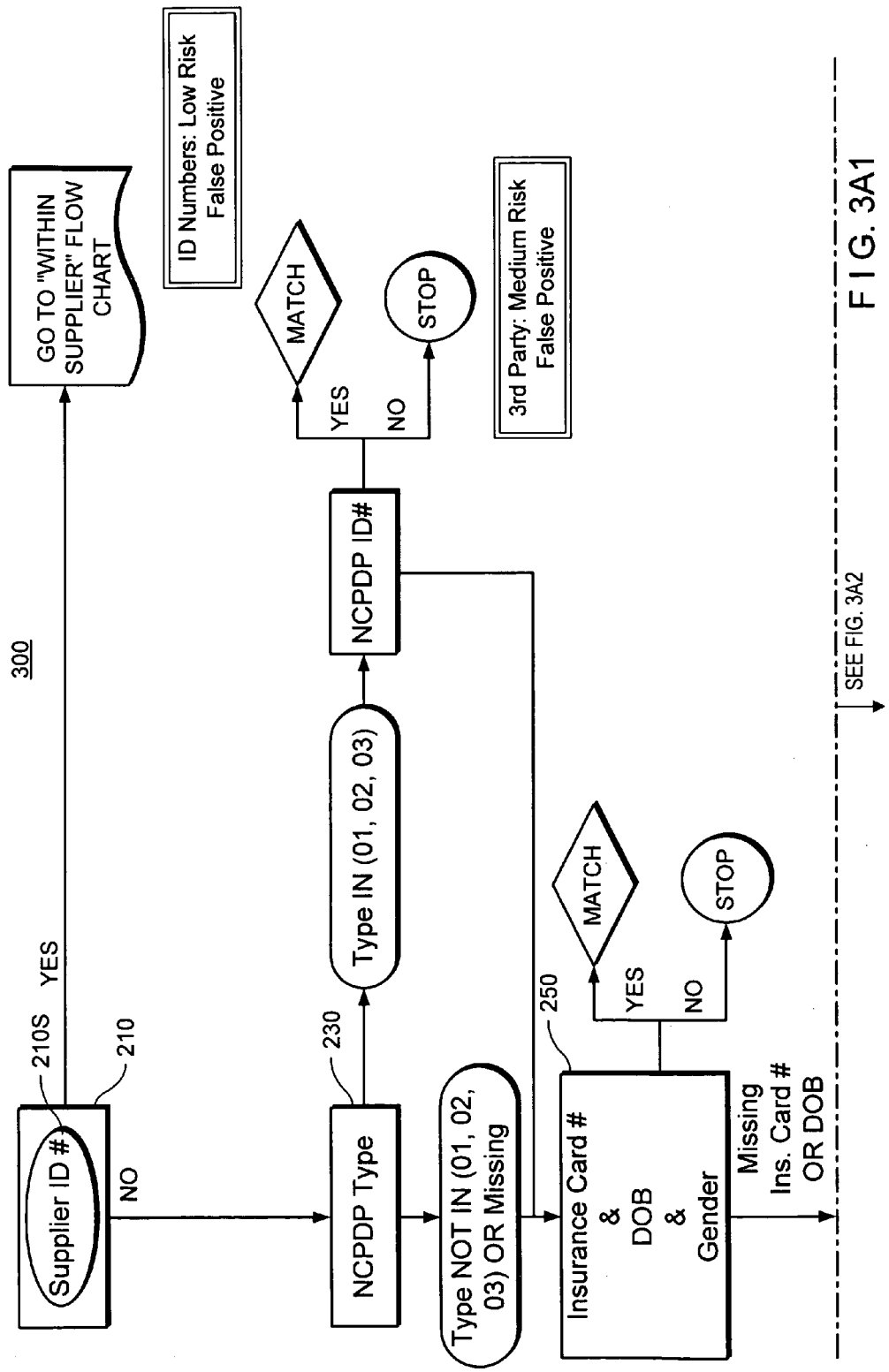
FIG. 3A1

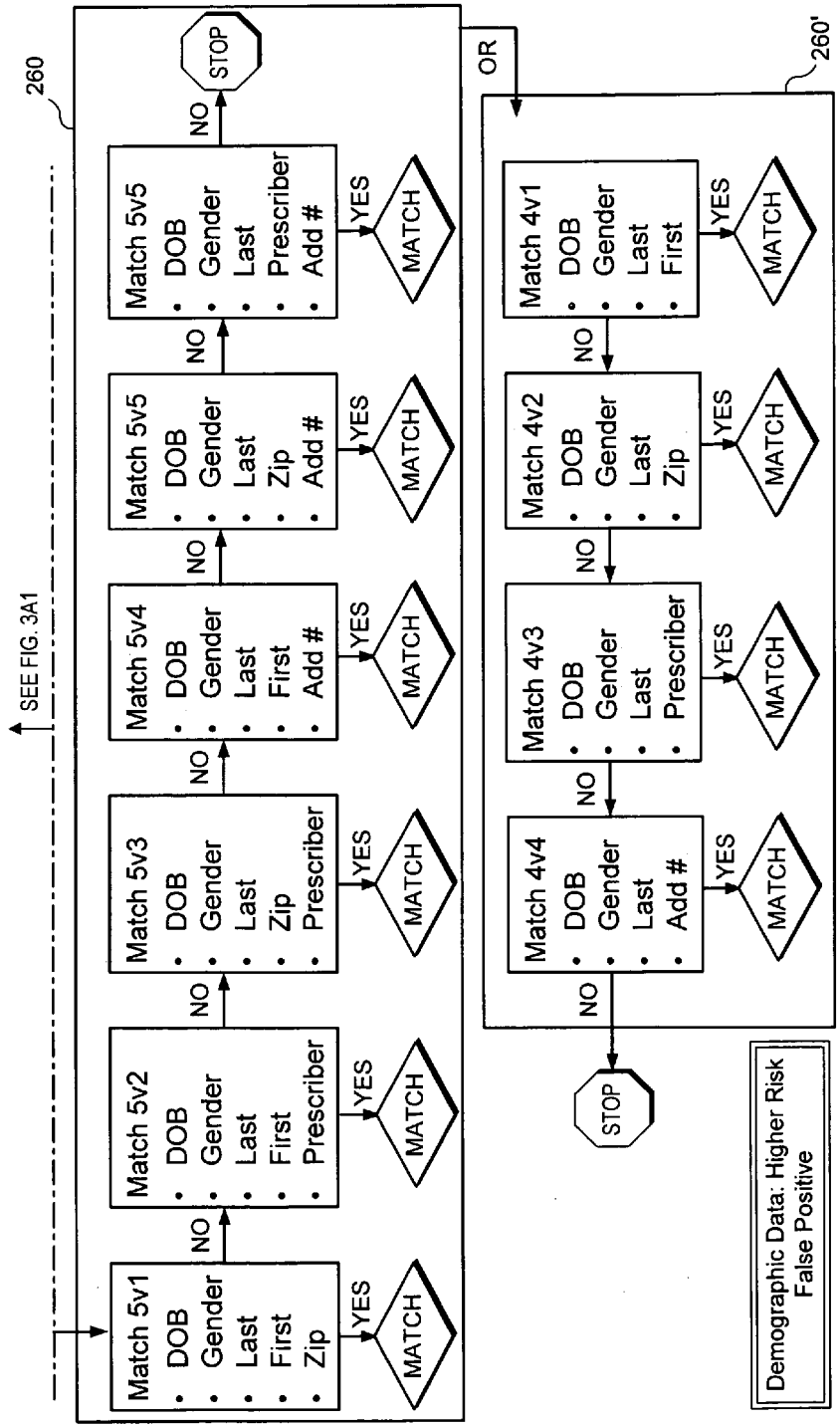
FIG. 3A2

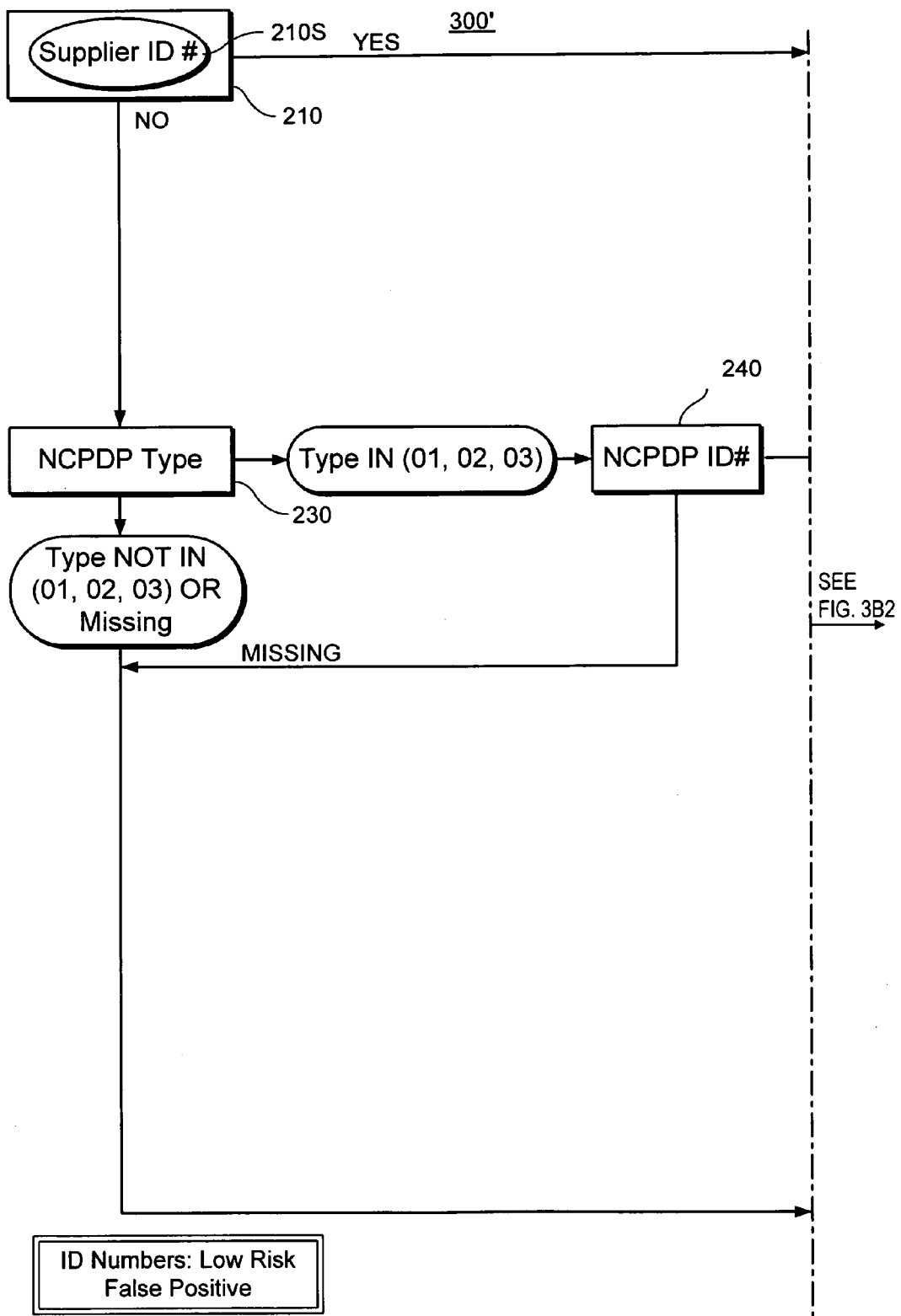
FIG. 3B1

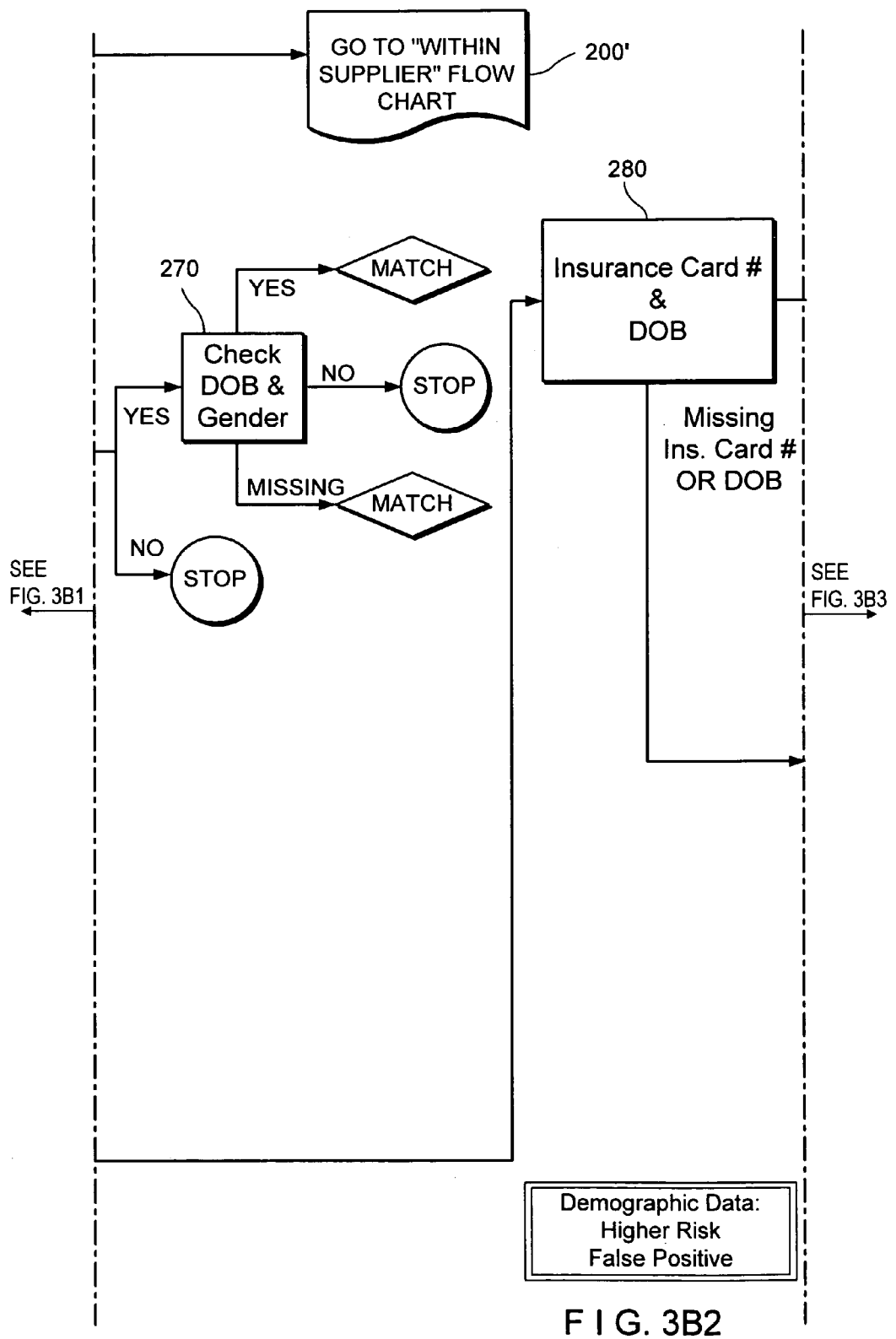
FIG. 3B2

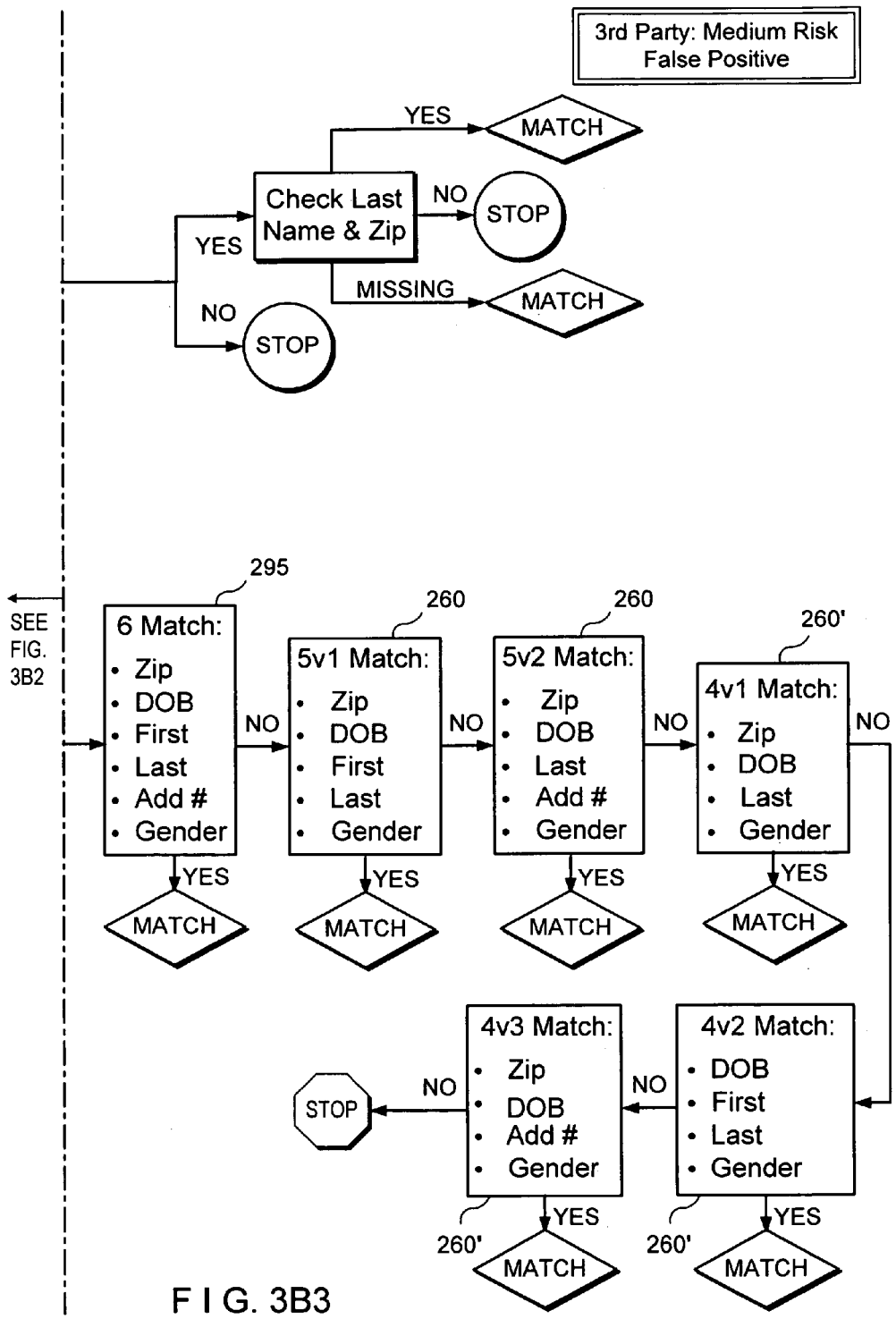
FIG. 3B3

| 1 | 2 | 3 | 4 | 5 | 6 | 7 |
|---|---|---|---|---|---|---|
| IF | ELSEIF | ELSEIF | ELSEIF | ELSEIF | ELSEIF | ELSEIF |
| PatID IR <> I or B | Supplier ID IR <> I or B | Supplier ID IR <> I or B | NCPDP Qualifier IR <> I or B | Full DOB IR = I | Insurance ID IR <> I or B | Insurance ID IR <> I or B |
| & | & | & | & | OR | & | & |
| Supplier ID IR = Supplier ID MDR 30 | PatID IR <> or I B | Outlet IR <> I or B | NCPDP ID IR <> I or B | Full DOB IR = B | Gender IR <> I or B | Gender IR <> I or B |
| & | & | & | & | | & | & |
| PatID IR = PatID MDR | Supplier ID IR= Supplier ID MDR | Rx# IR <> I or B | NCPDP Qualifier IR = NCPDP Qualifier MDR | | Patent Zip IR <> I or B | DOB IR = DOB MDR |
| | & | & | & | | & | & |
| | Outlet IR + Outlet MDR | Supplier ID IR = Supplier ID MDR | NCPDP ID IR + NCPDP ID MDR | | PatLN IR <> I or B | Insurance ID IR = Insurance Id MDR |
| | & | & | | | & | & |
| | PatID IR = Pat ID MDR | Outlet IR = Outlet MDR | | | PatFN IR <> I or B or S | Gender IR = Gender MDR |
| | | & | | | & | |
| | | RX# IR = RX# MDR | | | PatAdd# IR <> I or B | |
| | | | | | & | |
| | | | | | DOB IR = DOB MDR | |
| | | | | | & | |
| | | | | | Insurance ID IR = Insurance ID MDR | |
| | | | | | & | |
| | | | | | Gender IR = Gender MDR | |
| | | | | | & | |
| | | | | | Patient Zip IR = Patient Zip MDR | |
| | | | | | & | |
| | | | | | PatLN IR = Pat LN MDR | |
| | | | | | & | |
| | | | | | PatFN IR = Pat FN MDR | |
| | | | | | & | |
| | | | | | PatAdd# IR = PatAdd# MDR | |
| THEN | THEN | THEN | THEN | THEN | THEN | THEN |
| OLD | OLD | OLD | OLD | OLD | OLD | OLD |

Key: MDR = Matching Database Record, IR = Incoming Record, PatID = Patient ID#, PatLN = Patient Last Name, PatFN = Patient First Name, PatAdd# = Patient Address #, <> Implies Not Equal

FIG. 4

| 7 | 8a | 8b | 8c | 8d | 8e | 9 |
|---|---|---|---|---|---|---|
| ELSEIF | ELSEIF | ELSEIF | ELSEIF | ELSEIF | ELSEIF | ELSE |
| Insurance ID IR <> I or B | Gender IR <> I or B | Gender IR <> I or B | Gender IR <> I or B | Gender IR <> I or B | Patent Zip IR <> I or B | |
| & | & | & | & | & | & | |
| Gender IR <> I or B | Patent Zip IR <> I or B | Patent Zip IR <> I or B | Patent Zip IR <> I or B | PatLN IR <> I or B | PatLN IR <> I or B | |
| & | & | & | & | & | & | |
| DOB IR = DOB MDR | PatLN IR <> I or B | PatLN IR <> I or B | PatFN IR <> I or B or S | PatFN IR <> I or B or S | PatFN IR <> I or B or S | |
| & | & | & | & | & | & | |
| Insurance ID IR = Insurance Id MDR | PatFN IR <> I or S | PatAdd# IR <> I or B | PatAdd# IR <> I or B | PatAdd# IR <> I or B | PatAdd# IR <> I or B | |
| & | & | & | & | & | & | |
| Gender IR = Gender MDR | DOB IR = DOB MDR | DOB IR = DOB MDR | DOB IR = DOB MDR | DOB IR = DOB MDR | DOB IR = DOB MDR | |
| | & | & | & | & | & | |
| | Gender ID = Gender MDR | Gender ID = Gender MDR | Gender ID = Gender MDR | Gender ID = Gender MDR | Patent Zip IR = Patent Zip MDR | |
| | & | & | & | & | & | |
| | Patent Zip IR = Patent Zip MDR | Patent Zip IR = Patent Zip MDR | Patent Zip IR = Patent Zip MDR | PatLN IR = PatLN MDR | PatLN IR = PatLN MDR | |
| | & | & | & | & | & | |
| | PatLN IR = Pat LN MDR | PatLN IR = Pat LN MDR | PatFN IR = Pat FN MDR | PatFN IR = Pat FN MDR | PatFN IR = Pat FN MDR | |
| | & | & | & | & | & | |
| | PatFN IR = Pat FN MDR | PatAdd # IR = PatAdd# MDR | PatAdd # IR = PatAdd# MDR | PatAdd # IR = PatAdd# MDR | PatAdd # IR = PatAdd# MDR | |
| THEN | THEN | THEN | THEN | THEN | THEN | |
| OLD | OLD | OLD | OLD | OLD | OLD | NEW |

Key: MDR = Matching Database Record, IR = Incoming Record, PatID = Patient ID#, PatLN = Patient Last Name, PatFN = Patient First Name, PatAdd# = Patient Address #, <> Implies Not Equal

FIG. 4 (continued)

METHOD FOR LINKING DE-IDENTIFIED PATIENTS USING ENCRYPTED AND UNENCRYPTED DEMOGRAPHIC AND HEALTHCARE INFORMATION FROM MULTIPLE DATA SOURCES

CROSS REFERENCE TO RELATED APPLICATIONS

This application claims the benefit of U.S. provisional patent application Ser. No. 60/591,734 filed Jul. 28, 2004 and related U.S. patent application Ser. No. 11/122,589, Ser. No. 11/122,581, and Ser. No. 11/122,564, Ser. No. 11/122,565 all filed May 5, 2005. All of the aforementioned patent applications are hereby incorporated by reference herein in their entireties.

BACKGROUND OF THE INVENTION

The present invention relates to the management of personal health information or data on individuals. The invention in particular relates to the assembly and use of such data in a longitudinal database in manner that maintains individual privacy.

Electronic databases of patient health records are useful for both commercial and non-commercial purposes. Longitudinal (life time) patient record databases are used, for example, in epidemiological or other population-based research studies for analysis of time-trends, causality, or incidence of health events in a population. The patient records assembled in a longitudinal database are likely to be collected from a multiple number of sources and in a variety of formats. An obvious source of patient health records is the modern health insurance industry, which relies extensively on electronically communicated patient transaction records for administering insurance payments to medical service providers. The medical service providers (e.g., pharmacies, hospitals or clinics) or their agents (e.g., data clearing houses, processors or vendors) supply individually identified patient transaction records to the insurance industry for compensation. The patient transaction records, in addition to personal information data fields or attributes, may contain other information concerning, for example, diagnosis, prescriptions, treatment or outcome. Such information acquired from multiple sources can be valuable for longitudinal studies. However, to preserve individual privacy, it is important that the patient records integrated to a longitudinal database facility are "anonymized" or "de-identified".

A data supplier or source can remove or encrypt personal information data fields or attributes (e.g., name, social security number, home address, zip code, etc.) in a patient transaction record before transmission to preserve patient privacy. The encryption or standardization of certain personal information data fields to preserve patient privacy is now mandated by statute and government regulation. Concern for the civil rights of individuals has led to government regulation of the collection and use of personal health data for electronic transactions. For example, regulations issued under the Health Insurance Portability and Accountability Act of 1996 (HIPAA), involve elaborate rules to safeguard the security and confidentiality of personal health information. The HIPAA regulations cover entities such as health plans, health care clearinghouses, and those health care providers who conduct certain financial and administrative transactions (e.g., enrollment, billing and eligibility verification) electronically. (See e.g., http://www.hhs.gov/ocr/hipaa). Commonly invented and co-assigned U.S. patent application Ser. No. 10/892,021 filed Jul. 15, 2004, which is hereby incorporated by reference in its entirety herein, describes systems and methods of collecting and using personal health information in standardized format to comply with government mandated HIPAA regulations or other sets of privacy rules.

For further minimization of the risk of breach of patient privacy, it may be desirable to strip or remove all patient identification information from patient records that are used to construct a longitudinal database. However, stripping data records of patient identification information to completely "anonymize" them can be incompatible with the construction of the longitudinal database in which the stored data records or fields are necessarily updated patient by patient.

Commonly owned U.S. patent application Ser. No. 11/122,589 filed May 5, 2005, incorporated by reference herein, discloses a solution which allows patient data records acquired from multiple sources to be integrated each individual patient by patient into a longitudinal database without creating any risk of breaching of patient privacy.

The solution disclosed in the referenced patent application uses a two-step encryption procedure using multiple encryption keys. The procedure involves the data sources or suppliers ("DS"), the longitudinal database facility ("LDF"), and a third party implementation partner ("IP"). The IP, who may also serve as an encryption key administrator, can operate at a facility component site. At the first step, each DS encrypts selected data fields (e.g., patient-identifying attributes and/or other standard attribute data fields) in the patient records to convert the patient records into a first "anonymized" format. Each DS uses two keys (i.e., a vendor-specific key and a common longitudinal key associated with a specific LDF) to doubly encrypt the selected data fields. The doubly encrypted data records are transmitted to a facility component site, where the IP can process them further. The data records are processed into a second anonymized format, which is designed to allow the data records to be linked individual patient by patient without recovering the original unencrypted patient identification information. For this purpose, the doubly encrypted data fields in the patient records received from a DS are partially de-crypted using the specific vendor key (such that the doubly encrypted data fields still retain the common longitudinal key encryption). A third key (e.g., a token based key) may be used to further prepare the now-singly (common longitudinal key) encrypted data fields or attributes for use in a longitudinal database. Longitudinal identifiers (IDs) or dummy labels that are internal to the longitudinal database facility may be used to tag the data records so that they can be matched and linked individual ID by ID in the longitudinal database without knowledge of original unencrypted patient identification information. (See FIG. 1)

Commonly owned U.S. patent application Ser. No. 11/122,564 filed May 5, 2005, incorporated by reference herein, discloses matching algorithms, which may be used to determine if a new or previously defined ID should be assigned to a set of encrypted data attributes. Once a new or previously defined ID has been assigned, the ID may then be used to link back to tag full data records, which include detailed transaction information. The matching algorithms assign longitudinal linking tags to de-identified patient data records by matching the patient data records with reference data records. The de-identified patient data records may include both encrypted and non-encrypted data attributes. Different possible subsets of the data attributes are categorized in a hierarchy of levels. Subsets of data field values are compared with the reference data records one level at a time. Upon successful comparison or matching of a subset of data field values, a longitudinal linking tag associated with a matched reference data record is assigned to de-identified data record is assigned. When a match is not found, a new longitudinal linking tag is created and assigned to the de-identified data record. The new tag and corresponding data record attributes are then added to the reference data for future matching operations.

Further consideration is now being given to the processes for matching patient data generated or received from diverse data sources. In particular, attention is paid to matching processes and logic that, for example, allow linking of a patient's data records across different pharmacies serving the same patient.

SUMMARY OF THE INVENTION

The invention provides matching processes and algorithms for assembling longitudinal databases from multi-sources patient health care transaction records, which are de-identified to prevent unauthorized or inadvertent disclosure of patient identity or personal information. The de-identified patient healthcare transaction data records may include one or more data attributes such as alphanumeric identification code attributes, third party attributes and/or demographic attributes related to the patient healthcare transaction.

The matching processes and algorithms are designed to sequentially compare select sets of data attributes, which may include sets of demographic attributes, present in an incoming data record with corresponding sets of data attributes in existing reference data records. If a matching reference data record is found, the incoming data record is assigned the longitudinal linking tag which is associated with the matched reference data record.

In the matching processes, attempts are made to match incoming de-identified patient records (subject data records) to reference data records in an hierarchy of matching levels. At each matching level a designated set of data attributes is evaluated. Early matching levels involve comparison of alphanumeric identification codes (e.g., Supplier Patient ID, Supplier ID, Outlet ID and Rx Number) that may be included in a subject matching record. If the subject data record is not matched to a reference data record in these early matching levels, then the later matching levels may involve comparison of one or more demographic attributes (e.g., Insurance Card Number, DOB, Gender, Patient Zip, Last Name, First Name, Address No., etc.), which may be included in an subject matching record.

The hierarchy of matching levels and the associated sets of data attributes designated for comparison are selected with consideration of the matching effectiveness of particular data attributes or sets of data attributes. The matching effectiveness of particular data attributes or sets of data attributes may be determined empirically in trial runs using test data records.

An exemplary matching process, which may be implemented via suitable computer programs, is conducted in an hierarchy of levels (e.g., levels 1-13). At eleven of these levels (e.g., levels 1-4, and 6-12), the process attempts to match a de-identified patient record to a reference data record by comparing data attribute values. As soon as a match is found, the incoming record is assigned the matched record's longitudinal Patient ID and the matching process does not continue. At an intermediate level (e.g., level 5), the matching process may assess the incoming data record to verify the presence of relevant demographic data attributes (e.g. DOB) that may indicate the likelihood of matching success at subsequent matching levels. If such relevant demographic data attributes are the present, the matching process may continue through the remaining matching levels. In the case where an incoming data record does not match any existing reference data record, the incoming data record is assigned a newly generated internal identifier (e.g., at level 13).

The inventive matching processes can enrich the information content of longitudinal patient databases used in the healthcare or pharmaceutical industry (e.g., an LRx database). For example, de-identified Rx records of a de-identified patient who travels between two pharmacies can now be recognized or linked to the same ID. Previously, these Rx records may have been linked to two different persons. The LRx database may now be advantageously upgraded to include patient-centric metrics such as source of business (e.g., new start, restarts, continuing patients, etc.), treatment patterns (e.g., mono, combination, and add-on therapy), and therapy progressions (e.g., first, second, and third line, length of therapy, lapsed therapy/discontinued use, persistency and compliance, titration and dosing, and general patient characteristics).

BRIEF DESCRIPTION OF THE DRAWING

Further features of the invention, its nature, and various advantages will be more apparent from the following detailed description and the accompanying drawings, wherein like reference characters represent like elements throughout, and in which:

FIGS. 2a and 2b are schematic process flow diagrams illustrating the exemplary steps of processes for matching data records attribute level-by-level and for assigning longitudinal linking identifiers to the data records supplied by a particular data supplier, in accordance with the principles of the present invention;

FIGS. 3a and 3b are schematic process flow diagrams illustrating the exemplary steps of processes for matching data records attribute level-by-level and for assigning longitudinal linking identifiers to the data records supplied by multiple data suppliers, in accordance with the principles of the present invention; and FIG. 4, which also is reproduced from U.S. patent application Ser. No. 11/122,589, is an illustration of the logic of a software subroutine deployed for implementing the matching processes of FIGS. 2a, 2b, 3a and 3c, in accordance with the principles of the present invention.

DESCRIPTION OF THE INVENTION

Figure 1:
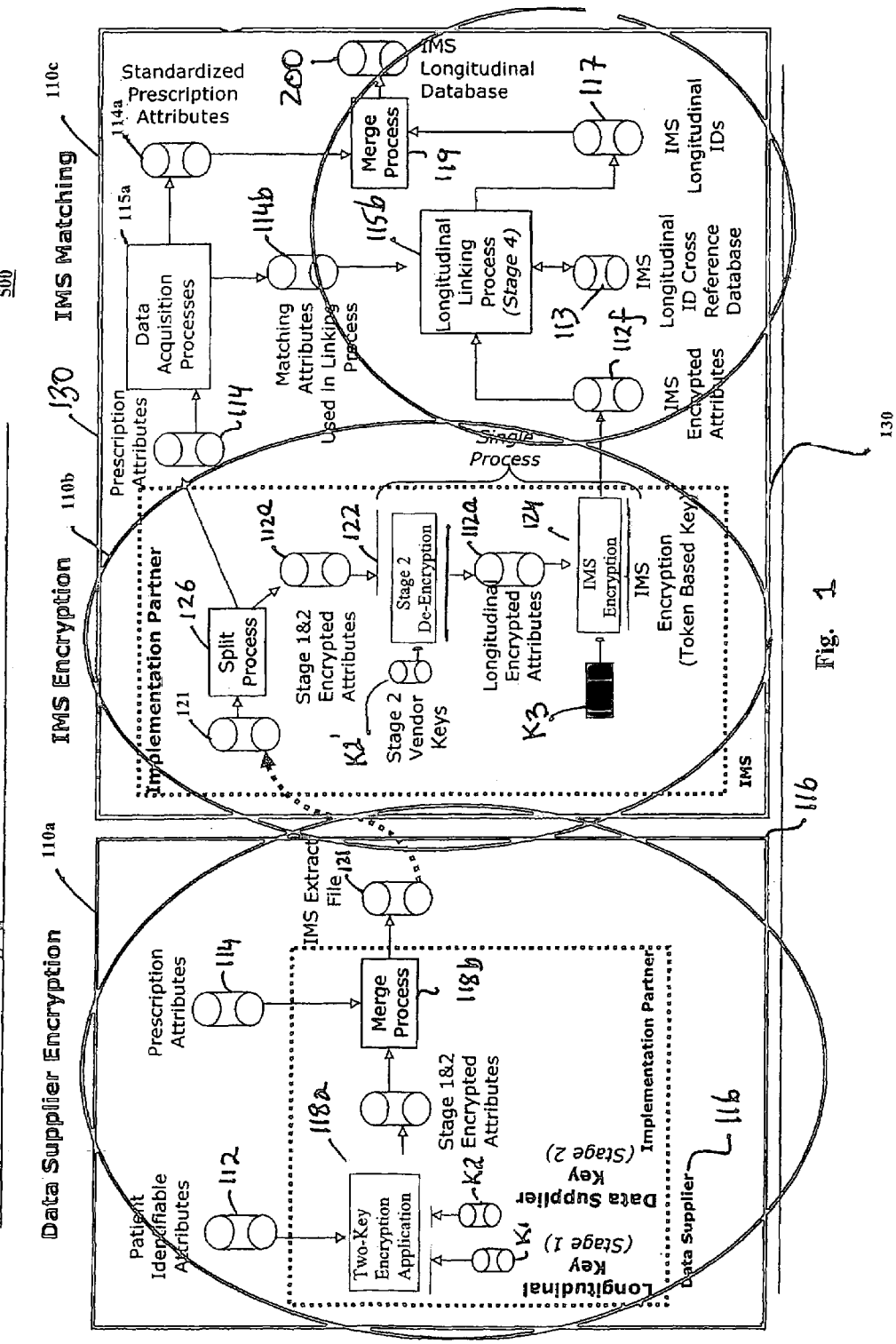
FIG. 1, which is reproduced from U.S. patent application Ser. No. 11/122,589, is a block diagram of an exemplary system for assembling a longitudinal database from multi-sourced patient data records. The matching processes of FIGS. 2a, 2b, 3a and 3b may be implemented in the system, in accordance with the principles of the present invention.

Matching algorithms are provided for assigning internal longitudinal linking identifiers or tags to de-identified patient transaction data records. Data records tagged with the assigned longitudinal linking identifiers may be readily linked identifier-by-identifier to assemble a longitudinal database without accessing personal information that can identify individual patients. The matching algorithms may be used to determine if a new or previously defined ID should be assigned to a set of encrypted data attributes. Once a new or previously defined ID has been assigned, the ID may then be used to link back to tag full data records, which include detailed transaction information.

For assembly in the longitudinal database, patient transaction data records are first processed so that the data fields in the data records are in a standardized common format and then encrypted. The data records include at least one or more data fields corresponding to a select set of data attributes. The select set of data attributes may include transaction attributes which when not encrypted are patient identifying as well other transaction attributes which are not patient-identifying. The inventive matching algorithms evaluate the values of the encrypted attributes in the data record and accordingly assign an internal longitudinal linking identifier to the data record. The evaluation may involve iteration, reference comparison, probabilistic or other statistical techniques for assigning a suitable longitudinal linking identifier. The select set of data attributes, which are evaluated, is chosen with a view to reduce errors in assigning proper longitudinal linking identifier to the data records.

The inventive matching algorithms are described herein with reference to their application in the context of an illustrative solution, (which is described in U.S. patent application Ser. No. 11/122,589, incorporated by reference herein) for integrating multi-sourced patient data records individual patient-by-patient into a longitudinal database without risking breach of patient privacy. It will be understood that the specific solution is referenced for purposes of illustration only, and that the inventive matching algorithms may readily find application in other solutions for integrating de-identified data records in a longitudinal database.

In order that the invention herein described can be fully understood, a brief description of the solution described in the referenced application is provided herein. FIG. 1, which is reproduced from the referenced application, shows system components and processes of an exemplary solution 100 for assembling a longitudinal database from multi-sourced patient data records. A two-step encryption procedure using multiple encryption keys is employed to de-identify patient data records. Solution 500 involves data sources or suppliers ("DS"), a longitudinal database facility ("LDF"), and a third party implementation partner ("IP") and/or key administrator. At the first step, each DS encrypts selected data fields (e.g., patient-identifying attributes and/or other standard attribute data fields) in the patient records to convert the patient records into a first "anonymized" format. Each DS uses two keys (i.e., a vendor-specific key and a common longitudinal key associated with a specific LDF) to doubly encrypt the selected data fields. The doubly encrypted data records are transmitted to a facility component site, where they are processed further. The data records are processed into a second anonymized format, which is designed to allow the data records to be effectively linked individual patient-by-patient without recovering the original unencrypted patient identification information.

For this purpose, the doubly encrypted data fields in the patient records received from a DS are partially de-crypted using the specific vendor key (such that the doubly encrypted data fields still retain the common longitudinal key encryption). A third key (e.g., a token based key) may be used to further prepare the now-singly (common longitudinal key) encrypted data fields or attributes for use in a longitudinal database. Longitudinal identifiers (IDs) or dummy labels that are internal to the LDF may be used to tag the data records so that they can be matched and linked individual ID-by-ID in the longitudinal database without knowledge of original unencrypted patient identification information.

Suitable matching algorithms may be used to determine if a previously defined or new ID should be assigned to a set of encrypted data attributes. Once an ID has been determined, the ID is then linked back to the detailed transaction records from the data supplier using a set of agreed upon matching attributes that have been passed through the process along with the encrypted attributes. The encrypted data attributes and the assigned ID are then stored within a reference database for use in future matching processes.

According to the present invention, a select set of data attributes/fields in a data record are used for matching incoming data records with reference data records stored in the longitudinal reference data base for purposes of assigning IDs to the incoming data records. The selected set of data attributes/fields may include data attributes/fields in addition to those that are designated to contain personal information. Matching rules and processes are provided for matching the incoming data records incrementally level by level (i.e. attribute by attribute). The matching rules and processes allow a patent's records, which are received from unrelated pharmacies or vendors, to be linked.

Traditional matching processes that use few encrypted patient variables (e.g., de-identified patient ID from the outlet (e.g., a retail pharmacy), the patient gender and the patient birth year) can be used to link patient records within an outlet by matching on de-identified patient IDs only. The inventive matching processes use an additional number of now available encrypted de-identified patient data attributes (e.g., full Date of Birth, Insurance Card ID, Last Name, First Name, Zip Code, etc.). These encrypted variables enable linkage of de-identified patient records across outlets, suppliers, and other data sources. The inventive matching processes are able to identify and link a patient's data records even if the patient moves or changes their last name.

In an exemplary matching process, attempts are made to match an incoming de-identified patient record with existing data records in a reference database. The attempts may be made sequentially in a hierarchy of matching levels (e.g., thirteen levels). At each of the exemplary thirteen levels in the hierarchy, attempts are made to match an incoming de-identified patient record to a record in the reference database (i.e., to associate the incoming de-identified patent record with an existing longitudinal ID). If there is a successful match, the de-identified patient record is assigned the ID associated with the matched reference data record. If there is no successful match, the de-identified patient record may be assigned a new patient ID ("longitudinal ID"). Each of the matching levels uses a different combination of data attributes to link or match a de-identified patient record to a longitudinal ID. Table I lists an exemplary set of pharmaceutical data attributes that may be included in the patient record data records that can be assigned IDs and linked by the process.

TABLE 1

Exemplary Sets of Attributes used in the Matching Logic

| Attribute | Encrypted | Description |
| --- | --- | --- |
| Supplier Patient ID | No | Patient ID created by the supplier, can be unique at the outlet level or at the supplier level. |
| Supplier ID | No | Supplier ID created by IMS. |
| Outlet | No | Outlet (store) number created by IMS. |
| Rx # | No | Prescription number assigned at the outlet. |
| NCPDP Qualifier[1] | No | Qualifier identifies whether the NCPDP ID is a social security number, military ID number, drivers license number or other. |
| NCPDP ID | Yes | Unique ID to an individual (based on Qualifier) |
| Patient Full Date of Birth (DOB) | Yes | Demographic variable. |
| Patient Insurance Card ID | Yes | Demographic variable. |

TABLE 1-continued

Exemplary Sets of Attributes used in the Matching Logic

| Attribute | Encrypted | Description |
|---|---|---|
| Patient Gender | No | Demographic variable. |
| Patient Zip - 5 digit | Yes | Demographic variable. |
| Patient Last Name | Yes | Demographic variable. |
| Patient First Name | Yes | Demographic variable. |
| Patient Address Number | Yes | Demographic variable that is created by searching the address line for the first appearance of a set of numbers. ("1245 Main St" becomes "1245"). |

[1]NCPDP = National Council for Prescription Drug Programs. Provides definitions for standard variables used in pharmacies.

Some of the thirteen data attributes listed in Table 1 (e.g., Supplier Patient ID, Supplier ID, Outlet and Rx #) may be attributes that do not reveal or at least do not directly reveal patient identifying information. The values of these attributes need not be encrypted in the data records. Other attributes may relate to sensitive patient-identifying information (e.g., NCPDP ID, Patient Full Date of Birth (DOB), Patient Insurance Card ID, Patient Gender, Patient Zip—5 digit, Patient Last Name, Patient First Name, and Patient Address Number). The values of such attributes are encrypted in the data records. All encrypted data fields/attributes may have a suitable standard format before they are encrypted. For example, missing and invalid values may be identified and coded with the characters "B" or "I", respectively. Special characters such as "&," "%", "{", and """, etc. may be removed from the data records. Leading blanks or zeros may be removed and data fields left or right justified. Further, all characters may be forced to upper case (or lower case).

FIGS. 2a and 2b show steps of exemplary "within supplier" matching processes 200 and 200' that can be used for assigning IDs to patient transaction data records acquired from a particular data supplier. A supplier ID number (e.g., Supplier ID 210S) may be used to identify the particular data supplier. Matching processes 200 and 200' may be implemented in the context of any suitable solution for assembling a longitudinal database (e.g. solution 100, FIG. 1). Matching processes 200 and 200' are designed to process an incoming patient transaction data record, which may include data supplier encrypted attributes and other data supplier standardized attributes. The incoming patient transaction data record may include some or all of the thirteen attributes shown in Table 1 and additionally include other attributes that are not shown in Table 1. The specific attributes included the data record may depend on the data supplier preferences or capability. Matching processes 200 and 200' compare an incoming data record with reference data records stored in a reference database. If a number of statistically significant data attributes/fields in the incoming data record match corresponding data attributes/fields in a particular reference record, then the incoming data record is assigned the ID associated with the particular reference record.

Matching processes 200 and 200' may be understood from FIG. 2a with reference to Table 2. Table 2 lists thirteen exemplary combinations of attributes (Match Levels 1-13) of incoming data records that may be compared with corresponding combinations in the reference data records in the reference database. The Levels are designed so that data records can be matched in a statistically valid manner. Levels 1-4 may attempt matches on attributes such as unique numeric or alphanumeric identification codes that are used to designate individual patients, data suppliers, stores and other parties in the data records. Levels 1-3 may attempt to match within an individual data supplier's patients. Level 4 may attempt matches both within and across data suppliers. Level 5 may determine if the incoming record includes sufficient demographic data or information to proceed with the matching process. If it does not, then the matching attempts may be discontinued and a new longitudinal ID may be assigned to the incoming record. If the incoming record includes sufficient demographic data, then the record proceeds to the higher matching levels. Levels 6-12 involve matching attempts across data suppliers based on various combinations of demographic variables. For most of these levels, an incoming record must match on at least 5 out of 7 demographic variables. The only exception is level 7 at which an incoming record can match on only 3 variables because level 7 uses insurance card, which is more unique than the other demographic variables. If an incoming de-identified patient record is not successfully matched by level 12, it may then be assigned or associated with a new longitudinal/patient ID.

TABLE 2

Hierarchy Match Level Descriptions

| Match Level | Incoming record matches the database on the following variables: | Description |
|---|---|---|
| 1 | Supplier Patient ID<br>Supplier ID | This level identifies matches within suppliers that have unique patient IDs across supplier (Examples: Rite-Aid). |
| 2 | Supplier Patient ID<br>Supplier ID<br>Outlet | This level identifies matches within suppliers that have unique patient IDs at an outlet. |
| 3 | Supplier ID<br>Outlet<br>Rx # | This level identifies matches within a supplier that does not use a unique patient ID system. |
| 4 | NCPDP Qualifier<br>NCPDP ID | This level identifies matches across all suppliers where patients have provided their social security number, military ID number, or drivers license number (NCPDP Qualifier must equal "01", "02", or "03"). Currently these variables are usually missing. |
| 5 | Patient Full Date of Birth | Level 5 is different from the other levels. It checks to ensure Full Date of Birth is populated before allowing the incoming record to proceed to levels 6 through 13. If date of birth is missing or invalid, then the record is given a new IMS patient ID. Otherwise, the record proceeds to Level 6. |

TABLE 2-continued

Hierarchy Match Level Descriptions

| Match Level | Incoming record matches the database on the following variables: | Description |
|---|---|---|
| 6 | Patient Full Date of Birth<br>Patient Insurance Card ID<br>Patient Gender<br>Patient Zip Code - 5 digit<br>Patient Last Name<br>Patient First Name<br>Patient Address Number | This level identifies a match across all suppliers where the 7 demographic variables are equal. |
| 7 | Patient Full Date of Birth<br>Patient Insurance Card ID<br>Patient Gender | This level identifies a match using only 3 demographic variables (one of them a numeric, highly unique variable). It can capture changes in last name and address. |
| 8 | Patient Full Date of Birth<br>Patient Gender<br>Patient Zip Code - 5 digit<br>Patient Last Name<br>Patient First Name | This level identifies a match using 5 demographic variables. It can capture changes in insurance card ID and address. |
| 9 | Patient Full Date of Birth<br>Patient Gender<br>Patient Zip Code - 5 digit<br>Patient Last Name<br>Patient Address Number | This level identifies a match using 5 demographic variables. It can capture changes in insurance card ID. |
| 10 | Patient Full Date of Birth<br>Patient Gender<br>Patient Zip Code - 5 digit<br>Patient First Name<br>Patient Address Number | This level identifies a match using 5 demographic variables. It can capture changes in insurance card ID and last name. |
| 11 | Patient Full Date of Birth<br>Patient Gender<br>Patient Last Name<br>Patient First Name<br>Patient Address Number | This level identifies a match using 5 demographic variables. It can capture changes in insurance card ID and zip code. |
| 12 | Patient Full Date of Birth<br>Patient Zip Code - 5 digit<br>Patient Last Name<br>Patient First Name<br>Patient Address Number | This level identifies a match using 5 demographic variables. It can capture changes in insurance card ID. |
| 13 | None | This level identifies a record that did not match to the patient database. A new IMS patient ID is assigned. |

The data attributes are evaluated combination by combination in a hierarchical sequence (i.e. level by level) until a match is found. It will be understood that the particular combination of attributes listed in Table 1 is exemplary. Various implementations of data record matching processes may use some or all of these combinations and/or other combinations as desired or appropriate.

With reference to FIG. 2a, at a preliminary step 210 in matching process 200, the Supplier ID attribute encoded in an incoming "subject" data record is compared with Supplier ID 210s that is associated with the particular data supplier. If the subject data record is not encoded with Supplier ID 210s, then the subject data record is transferred to matching process 300 (FIG. 3a), which can match patient records across different data suppliers.

If the subject data record is encoded with Supplier ID 210s then at step 220, process 200 evaluates any patient identifier numbers that may be included in the subject data record by the data supplier (i.e. Supplier ID 210s). The data supplier may include a universal or "across supplier" patient identification number or other unique identification number to identify patient data records. The universal patient identification number if present in the subject data record is compared with those in the reference data records. If the universal patient identification number matches that of a reference data record a Level 1 match is declared. If the data supplier includes an outlet specific patient identification number instead of a universal patient identification number, then at step 220 the outlet specific patient identification number and outlet attributes in the subject data record are compared with those of the reference data records. Upon successful matching of these two data attributes a Level 2 match is declared. Alternatively at step 220, for data from suppliers who do not use either a universal or outlet-specific patient identification numbers in the data records, process 200 may be configured to declare a Level 3 match at step 220 upon successful comparison of outlet and prescription number attributes in the subject data record with those in a reference data record. For successful Level 1, 2 or 3 matches, the subject data record is assigned the longitudinal ID associated with the matched reference data record. When no matches to a reference data record are obtained at step 220, process 200 attempts matching at higher levels.

At step 230, process 200 determines the NCPDP qualifier of any NCPDP patient ID that may be present in the subject data record. If the NCPDP qualifier is a standard insurance type 01, 02 or 03 (e.g., corresponding to social security number, military ID number, or drivers license number, respectively) then at step 240, process 200 compares the NCPDP patient ID present in the subject data record with those of the reference data records. Process 200 may be configured to declare a Level 4 match upon successful comparison of the NCPDP patient ID in the subject data record with that in a reference data record. If at step 230, process 200 determines an NCPDP patient ID is not present or is not of standard insurance type 01, 02 or 03 then process 200 may proceed to step 250 to evaluate additional data attributes (e.g., demographic data attributes), which may be present in the subject data record. For example, at step 250 a set of three attributes (e.g., Insurance Card number, Date of Birth (DOB) and Gender attributes) present in the subject data record may be compared with those in the reference data records. Process 200 may be configured to declare a Level 7 match upon successful comparison of these three attributes present in the subject data record with those in a reference data record. Process 200 may proceed to step 250 to evaluate additional data attributes only after confirming at a preliminary step (not shown) that the yet unmatched subject data record includes relevant or critical additional data attributes (e.g., a DOB attribute).

The set of three attributes used at step 250 includes attributes such as Insurance Card Number and DOB, which have numerical values. For processing subject data records that do not include one of these attributes (i.e., the Insurance Card Number is missing), process 200 attempts to match the subject data record based on additional data attributes that are now commonly included in the patient transaction records obtained from data suppliers. At step 260, process 200 attempts matching the subject data record by sequentially comparing values of sets of five demographic attributes that may be present in the subject data record with those in the reference data records. Exemplary sets of five demographic variables commonly include three attributes (i.e., DOB, Gender, and Last Name attributes) and two additional attributes selected from the group of four attributes (First Name, Zip Code, Prescriber Name, and Address Number). FIG. 2a shows six such sets of five data attributes, which are sequentially used to match the subject data records. Process 200 may be configured to declare a match (e.g., levels 8-12 or higher) upon successful comparison of any such set of five data attributes present in the subject data record with those in a reference data record.

Alternatively, process 200 may be configured to match the subject data record at modified step 260' by sequentially comparing values of sets of four demographic attributes which may be present in the subject data record with those in the reference data records. The exemplary sets of four demographic variables may commonly include three attributes (DOB, Gender, and Last Name) and one additional attribute selected from the group of four attributes (First Name, Zip Code, Prescriber Name, and Address Number). FIG. 2a shows four such sets of four data attributes, which are sequentially used to match the subject data records. Process 200 may be configured to declare a match upon successful comparison of any such set of four data attributes present in the subject data record with those in a reference data record.

If no successful match is found at steps 210-260 or 260', process 200 is configured to recognize the subject data record as belonging to a new patient and to according assign a new ID tag to the subject data record. The new ID tag can be used to link the subject data record to subsequently matched data records in the longitudinal database.

In process 200, steps 210-230, which involve matching based on numerical or alphanumeric identification code attributes, present a low risk of false positive results. Step 250, which involves matching based on third party data (e.g., Insurance Card Number), presents a moderate risk of false positive results. Step 260, which involves matching based demographic data, has an increased risk of false positive results. The matching process 200 is compatible with privacy requirements so that at no stage of the data processing, the LDF (or any other unauthorized entity) is able to view patient identifiable data. For example, the LDF may know that a patient (identified only by a longitudinal ID, e.g., Mr. XXY&^% FR21gywt30 Jjokiau76gfs545a) has traveled to multiple pharmacies or stores. However, the LDF will not know or be able to identify a particular "Mr. John Smith" as having traveled to multiple stores.

FIG. 2b shows another matching process 200' that may be used to process subject data record for inclusion in a longitudinal data base. Processes 200' uses different combinations of demographic data attributes and a different logical flow of matching steps than process 200 to assign an ID to a subject data record. Process 200' like process 200 is designed to process data records from a particular data supplier (e.g., Supplier ID 210S) but includes additional process steps to verify successful matches. In process 200' steps 210-240, which like similar steps in process 200 involve investigation of data attributes having alphanumerical identification codes as values, are followed by a confirming step 270. Any successful matching of the subject data record to a reference data record at steps 210-240 is verified at step 270 by checking that the DOB and Gender attributes of the subject data record are the same as those in the matched reference data record.

Further, if at step 230 process 200' determines an NCPDP patient ID is not present or is not of standard insurance type 01, 02 or 03 then process 200' proceeds to steps 245-295, 260 and 260' to evaluate additional sets of data attributes which may be present in the subject data record. The sets of data attributes investigated at steps 245-295, 260 and 260' may be different than those investigated at steps 250-260' in process 200. At step 245, process 200' attempts to match Outlet Identification and Store Specific Patient Identification attributes, which may be present in the subject data record. At step 255, process 200' attempts to match Outlet Identification and Prescription Number attributes, which may be present in the subject data record patient. Successful matches at both steps are further verified at a confirming step 270 before a successful match is declared.

For further processing a subject data record that does not include at least one of Outlet Identification and Prescription Number attributes, process 200 at step 280 attempts to match the subject data record by evaluating a set of three attributes (Insurance Card Number, DOB and Gender). If any matching reference data record is found, then process 200' at step 290 confirms that matching reference data record and the subject data record have the same Last Name and Zip Code attributes before declaring a successful match.

In instances where the subject data record does not include an Insurance Card Number attribute, process 200' attempts to match the subject data record based on additional demographic attributes which may be present in the subject data record. At step 295, process 200' attempts matching the subject data record to a reference data record by comparing values of a set of six data attributes (e.g., Zip Code, DOB, First Name, Last Name, Address, Number and Gender). At steps 260 and 260,' process 200' like process 200 attempts to match the subject data record to a reference data record by comparing values of a sets of five and four data attributes, respectively. The sets of five data attributes at step 260 commonly include three data attributes namely Zip Code, DOB and Gender. The remaining two attributes in the sets of five data attributes are selected as a pair from First Name, Last Name, and Address Number attributes. The sets of four data attributes at step 260' commonly include two data attributes namely DOB and Gender. The other pair of attributes in the sets of four data attributes is selected as one of the pairs (Zip Code, Last Name), (Zip Code, Address Number) or (First Name, Last Name).

Matching processes 200 and 200' are designed for processing subject data records received from a particular data supplier. Matching processes may also be designed to process and assign suitable longitudinal IDs to multi-sourced subject data records which may be received from any number of data suppliers. FIGS. 3a and 3b show the exemplary steps of exemplary "across supplier" matching processes 300 and 300', respectively. Matching processes 300 and 300' use combinations of data attributes for data record matching similar to those used in matching processes 200 and 200', respectively. Matching processes 300 and 300' may be operated in conjunction with or as extensions of process 200 and 200', respectively.

Processes 300 and 300' may be initiated when preliminary steps 210 of process 200 and process 200' indicate that the subject data record is not encoded with a particular supplier's Supplier ID 210s. Unlike process 200 and 200', "across-supplier" processes 300 and 300' do not attempt to match the subject data record to a reference data record by comparing values of a Supplier Specific Patient Identifier attribute (See e.g., process 200 step 220). Apart from this difference, process 300 may use the same or similar sequential combinations or levels of attributes as process 200 (e.g., steps 230-260 and 260') in attempts to match the subject data record to a reference data record. Similarly, process 300' may use the same or similar sequential combinations or levels of attributes as process 200' (e.g., steps 230-295, 260 and 260') in attempts to match the subject data record to a reference data record.

Hierarchical matching processes (e.g., processes 200, 200', 300 and 300'), which are based on comparisons of multiple sets of attributes including demographic attributes, may be advantageously used to enhance the information content of longitudinal prescription databases (e.g., an LRx database). For example, de-identified Rx records of a de-identified patient who travels between two pharmacies can now be recognized or linked to the same ID. Previously, these Rx records may have been linked to two different persons. The LRx database may now be advantageously upgraded to include patient-centric metrics such as source of business (e.g., new start, restarts, continuing patients, etc.), treatment patterns (e.g., mono, combination, and add-on therapy), and therapy progressions (e.g., first, second, and third line, length of therapy, lapsed therapy/discontinued use, persistency and compliance, titration and dosing, and general patient characteristics). The matching logic and the additional encrypted attributes used in the hierarchical matching processes, improve the accuracy of the patient-centric metrics by linking de-identified patients who travel between pharmacies and healthcare facilities. The inventive matching processes are compatible with privacy requirements. The matching processes are designed so that at no stage of the data processing the LDF (or any other unauthorized entity) is able to view patient identifiable data. For example, the LDF may know that a patient (identified only by longitudinal ID or code, e.g., Mr. XXY&^% FR21gywt30 Jjokiau76gfs545a) has traveled to multiple stores. However, the LDF will not know or be able to identify a particular "Mr. John Smith" as having traveled to multiple stores.

It will be understood that combinations of attributes, the hierarchy of matching levels, and the matching logic used in matching processes may be suitably modified or changed as appropriate for meeting specific data processing requirements or circumstances, in accordance with the principles of the invention. The number of levels in the hierarchy of matching levels also may be changed. The matching logic and the number of levels may be modified (e.g., reduced) if it is determined that certain levels are inefficient (i.e. do not link many de-identified patients) or if it is determined that processing the levels in a different order would provide a more efficient process.

The development of a suitable matching process or algorithm for meeting specific data processing requirements or circumstances may be formulated as the problem of determining the best matching algorithm or the best way to uniquely identify individual patients from multi-sourced data records given a selected set of data attributes in the data records. For example, in the development of matching processes 200, 200', 300 and 300', an initial set of twelve data attributes was selected and tested for utility and efficiency in matching subject data records to reference data records. The initial set of twelve data attributes included standardized data attributes such as Cardholder ID, Full Date of Birth (DOB), Gender, First Name, Last Name, Address (cleaned, standardized), Zip Code—5 digit, NCPDP ID and NCPDP Qualifier, Rx #, Outlet, Supplier ID, Patient ID (from Pharmacy). Several of the data attributes (e.g., First Name, Last Name, Address and Patient ID) are routinely encrypted in data records obtained from healthcare data suppliers. The evaluation and development of the matching processes for deployment in the field included determinations of the effectiveness of supplier and other data encryption processes, and investigations to see if an address number attribute could be used instead of a full address attribute with positive results. Further, the matching process are designed to identify a patient who purchases prescriptions from two different pharmacies or outlets, either within or across a supplier, as one individual and not as two individuals.

In field implementations of the matching processes, the particular combinations of attributes or matching levels, the hierarchy of matching levels, and the matching logic deployed may be selected on theoretical or empirical considerations. The combinations and types of attributes utilized for matching may, for example, be selected according to their potential in matching subject data records with reference data records. The matching levels or combinations of attributes utilized in processes 200, 200', 300 and 300' were selected on the basis of such considerations. Tables 3 and 4 list the empirically determined matching usefulness or effectiveness of the sets of attributes used in processes 200, 200', 300 and 300' in matching subject data records to reference data records in the context of a longitudinal prescription database (LRx). Table 3 relates to "within supplier" data record matching situations (e.g., matching processes 200 and 200'), while Table 4 relates to "across supplier" data record matching situations (e.g., matching processes 300 and 300'). In both Tables, the data attributes and combination of attributes, which are used in the matching processes, are ranked according to matching potential (e.g., matching rank–best=1 to worst=9).

TABLE 3

LRx Patient ID Minimum Match "within supplier"

| Within Supplier | | Match Rank | Supplier ID (2-digit) | Supplier Specific Patient ID# | NCPDP ID# | NCPDP ID Qualifier | Insurance Card # | Patient DOB | Patient Gender | Last Name | First Name | Patient Zip Code | Prescriber | Address Numbers |
|---|---|---|---|---|---|---|---|---|---|---|---|---|---|---|
| ID #s | Best | 1 | X | X | | | | | | | | | | |
| | Match | 2 | X | | X | X | | | | | | | | |
| 3rd Party | | 3 | X | | | | X | X | X | | | | | |
| Patient | Worst | 4 | X | | | | | X | X | X | X | X | | |
| Demo- | Match | 5 | X | | | | | X | X | X | X | | X | |
| graphics | | 6 | X | | | | | X | X | X | X | | | X |
| | | 7 | X | | | | | X | X | X | | X | X | |
| | | 8 | X | | | | | X | X | X | | X | | X |
| | | 9 | X | | | | | X | X | X | | | X | X |
| ID #s | Best | 1 | X | X | | | | | | | | | | |
| | Match | 2 | X | | X | X | | | | | | | | |
| 3rd Party | | 3 | X | | | | X | X | X | | | | | |
| Patient | Worst | 4 | X | | | | | X | X | X | X | | | |
| Demo- | Match | 5 | X | | | | | X | X | X | | X | | |
| graphics | | 6 | X | | | | | X | X | X | | | X | |
| | | 7 | X | | | | | X | X | X | | | | X |

TABLE 4

LRx Patient ID Minimum Match "across supplier"

| Across Supplier | | Match Rank | Supplier ID (2-digit) | Supplier Specific Patient ID# | NCPDP ID# | NCPDP ID Qualifier | Insurance Card # | Patient DOB | Patient Gender | Last Name | First Name | Patient Zip Code | Prescriber | Address Numbers |
|---|---|---|---|---|---|---|---|---|---|---|---|---|---|---|
| ID #s | Best Match | 1 | | | X | X | | | | | | | | |
| 3rd Party | | 2 | | | | | X | X | X | | | | | |
| Patient | Worst | 3 | | | | | | X | X | X | X | X | | |
| Demo- | Match | 4 | | | | | | X | X | X | X | | X | |
| graphics | | 5 | | | | | | X | X | X | X | | | X |
| | | 6 | | | | | | X | X | X | | X | X | |
| | | 7 | | | | | | X | X | X | | X | | X |
| | | 8 | | | | | | X | X | X | | | X | X |
| ID #s | Best Match | 1 | | | X | X | | | | | | | | |
| 3rd Party | | 2 | | | | | X | X | X | | | | | |
| Patient | Worst | 3 | | | | | | X | X | X | X | | | |
| Demo- | Match | 4 | | | | | | X | X | X | | X | | |
| graphics | | 5 | | | | | | X | X | X | | | X | |
| | | 6 | | | | | | X | X | X | | | | X |

Either deterministic or probabilistic matching criteria or logic may be used in the matching processes to declare a successful comparison or match between two data records. Most patient demographic attributes in healthcare data records available for processing are encrypted. Further, it is difficult to judge situations where an attribute (e.g., Last Name) is sufficiently "close" in value to another attribute to be the same (e.g., Smith vs. Smyth). In such situations, use of probabilistic matching logic for comparing subject data record attributes with reference data record attributes is likely to lead to false positives. Therefore, the matching processes (e.g., processes 200, 200' 300 and 300') may be configured to use exact or deterministic matching logic to compare data attributes. Under such logic, two patient data records either match or not match in a binary fashion. The clear binary positive or negative results obtained using deterministic logic are advantageous for practical implementations of the matching processes. Further, investigations showed that the use an address number attribute instead of a full address attribute for data record comparison is advantageous for matching data records. The use of address numbers may reduce the data entry errors that can occur when entering a full address in a data record.

The matching level hierarchy in a matching process (e.g., processes 200, 200' 300 and 300') may be designed by selecting particular data attributes (or combinations of attributes), which when identical provide the best patient match. Better patient matches correspond to smaller likelihood of false positives. The matching levels in the hierarchy may be designed so that a minimum number of data attributes is needed or tested at each level. If a subject patient data record fails to match a reference patient data record at one level, then the matching process moves to the next level to search for a match. This implies that the lower the matching level number of a successful match, the better the match. Tables 3 and 4 identify the particular combinations of attributes that were found to be a minimum match requirement for declaring a successful data record match for "within supplier" and "across supplier" situations, respectively, in the context of prescription data records (e.g., LRx database). Additional or alternate combinations of attributes may be found to be suitable in other situations or circumstances. For example, in matching processes for linking prescription data records it may be useful to consider a "physician" attribute as a matching attribute.

The matching processes may be suitably designed to account for data processing situations in which a data attribute/field is invalid or missing from the subject data record in contrast to non-match situations. Table 5 is an exemplary list of data attributes whose values in two data records need not be the same (i.e., not match) even when the two data records belong to the same or identical patient. Table 5 also shows possible reasons why the data attributes in the two subject data records belonging to the same or identical patient can be different.

TABLE 5

Which attributes can change, but still be the same patient?

| Attribute | Change Reason |
|---|---|
| Insurance Card # | New insurance company |
| Patient Zip Code | Moved |
| Last Name | Married |
| First Name | Entered incorrectly??? |
| Address Numbers | Moved |

The matching processes may be implemented as a computer program. In accordance with the present invention, software (i.e., computer program instructions) for implementing the aforementioned matching processes can be provided on computer-readable media. It will be appreciated that each of the steps (described above in accordance with this invention), and any combination of these steps, can be implemented by computer program instructions. Any suitable computer programming language may be used for this purpose. FIG. 4 shows an implementation of a matching algorithm as an exemplary computer subroutine 400 for processing patient data records. In subroutine 400, matching rules are applied to select sets of data attributes as a series of nested IF-ELSE IF-THEN conditional statements, each of which corresponds to a level or combination of data attributes in the data records tested (See e.g., Table 1). The matching algorithm uses 13 variables in a hierarchy of 9 levels (13 combinations of variables).

The computer program instructions can be loaded onto a computer or other programmable apparatus to produce a machine, such that the instructions, which execute on the computer or other programmable apparatus create means for implementing the functions of the aforementioned matching processes. These computer program instructions can also be stored in a computer-readable memory that can direct a computer or other programmable apparatus to function in a particular manner, such that the instructions stored in the computer-readable memory produce an article of manufacture including instruction means which implement the functions of the aforementioned innervated stochastic controllers and systems. The computer program instructions can also be loaded onto a computer or other programmable apparatus to cause a series of operational steps to be performed on the computer or other programmable apparatus to produce a computer implemented process such that the instructions which execute on the computer or other programmable apparatus provide steps for implementing the functions of the aforementioned matching algorithms and processes. It will also be understood that the computer-readable media on which instructions for implementing the aforementioned matching algorithms and processes are provided, include without limitation, firmware, micro controllers, microprocessors, integrated circuits, ASICS, and other available media. A computer readable storage media and computer readable storage medium includes computer readable memory.

The programming logic of exemplary subroutine 400 assumes that the subject incoming patient record is compared to reference data records, which may be stored in a reference database. At each matching level (i.e., set of data attributes designated for comparison) subroutine 400 will scan the reference database to search for a matching reference data record. If no matching reference data record is found at any of the designated matching levels, subroutine 400 may determine that the subject incoming patient record should be associated with a new patient or ID.

Other programming implementations of the inventive matching processes may contain fewer levels or more levels than shown in FIG. 4. For example, Level 12 was removed from some field implementations of subroutine 400. Further, the programming implementations may include suitable routines designed to check the integrity of the incoming data records. For example, subroutine 400 may be modified or extended to include steps to identify invalid or missing data attributes in an incoming data record. Additionally, the programming implementations may be configured with tolerant matching logic to address common data processing issues. For example, the matching logic in the programming implementations may tolerate a change in a female patient's last name and positively match a data record having the patient's changed last name with a data record having her original last name.

The programming implementations of the inventive matching processes may be tested, evaluated, and optimized using test data from data supplier/vendors. Using test data from a single data supplier/vendor (e.g., McKesson) the matching logic of a programming implementation may be tested as follows:

Determine the levels with the most matches and change match level hierarchy as needed to speed up the match processing.

Determine how often each data attribute is equal to B, S, or I.

Determine if person code/relationship code would help the matching process.

Determine how many more matches are obtained by matching on individual elements as opposed to one longitudinal key created from the elements Determine how often an incoming record matches to more than one record in the a reference Patient Matching Database. This may help clarify how often the LDF should run a "clean-up."

Determine how often Last Name, Card ID, Address, and Zip attributes change for a single patient within a certain time period.

Using additional test data from a second data supplier/vendor (e.g., a Pharmacy Benefit Management (PBM) data supplier), the matching logic of a programming implementation may be further tested as follows:

Determine how often patients within certain geographies travel between the first and second data supplier/vendor stores.

Is this number realistic?

Is it similar to data obtained from other patient travel studies?

Scripts data (Rx scripts) received from a PBM may be processed, deduped and cleaned before it can be used as test data for evaluation of a programming implementation. The attributes needed to distinguish scripts data may include attributes such as Supplier ID, Outlet #, Insurance Company, Insurance Card Number, DOB, Last Name (Optional), First Name (Optional), Gender, and (Rx #, Date Filled, Physician) or (Drug #, Date Filled, Physician). The usefulness of PBM data (e.g., for matching patients across pharmacies) may depend on the data attributes provided by a PBM. For example, a PBM may provide Outlet-specific Rx #, Date Filled, Physician, Dependent DOB, and Gender data attributes. Accordingly, the matching logic used in the programming implementations may be based on evaluation of such data attributes. In practice, to determine the effectiveness of patient matching across data suppliers, attention may be directed to a particular set of attributes (e.g., State, County, MSA, Zip Code 5-digit and Zip Code 3-digit). The results of matching patients across pharmacies also may depend on whether an outlet can issue the same Rx number more than once a day.

In trial runs, the inventive matching algorithms (e.g. subroutine 400) were evaluated against test data sets (i.e., encrypted data records obtained from data suppliers PDX and McKesson). Tables 5-7, and 8A-8E show results from the trial runs.

Table 5 shows matching efficiency ranks for various combinations of data attributes that were used in the trial runs as minimum match requirements for assigning an LRx Patient ID. Tables 6 and 7 shows results of investigations and tests of various combinations of data attributes as potential basis for finding matching between two data records under common data processing conditions or scenarios.

TABLE 5

| | | | LRx Patient ID Minimum Match | | | | | | | | | | | | |
|---|---|---|---|---|---|---|---|---|---|---|---|---|---|---|---|
| | | Match Rank | Supplier ID (2-digit) | Supplier Specific Patient ID# | NCPDP ID# | NCPDP ID Qualifier | Outlet | Store-Specific Patient ID# | RX # | Insurance Card # | Patient Zip Code | Patient DOB | First Name | Last Name | Address Numbers | Patient Gender |
| Within Supplier | | | | | | | | | | | | | | | | |
| Type ID #s | Level Best Match | 1 | X | SP X | SP | ST | ST | ST | ST | ST | U | U | U | U | U | U |
| | | 2 | X | | X | X | | | | | | | | | | |
| | | 3 | X | | | | X | X | | | | | | | | |
| | | 4 | X | | | | X | | X | | | | | | | |
| 3rd Party Patient Demographics | Worst Match | 5 | X | | | | | | | X | | X | | | | |
| | | 6 | X | | | | | | | | X | X | X | X | X | X |
| | | 7 | X | | | | | | | | X | X | X | X | | X |
| | | 8 | X | | | | | | | | X | X | | X | X | X |
| | | 9 | X | | | | | | | | X | X | | X | | X |
| | | 10 | X | | | | | | | | X | X | X | X | | X |
| | | 11 | X | | | | | | | | X | X | | | X | X |
| Across Supllier | | | | | | | | | | | | | | | | |
| ID #s | Best Match | 12 | | | X | X | | | | | | | | | | |
| 3rd Party Patient Demographics | Worst Match | 13 | | | | | | | | X | | X | | | | |
| | | 14 | | | | | | | | | X | X | X | X | X | X |
| | | 15 | | | | | | | | | X | X | X | X | | X |
| | | 16 | | | | | | | | | X | X | | X | X | X |
| | | 17 | | | | | | | | | X | X | | X | | X |
| | | 18 | | | | | | | | | X | X | X | X | | X |
| | | 19 | | | | | | | | | X | X | | | X | X |

TABLE 6

Match Logic

| Level | Test | Record Matched/Not-Matched | Notes |
|---|---|---|---|
| 1 | Match on Rite-Aid type ID | Matched | Do we assume today that these IDs are correct? |
| 2 | Match on Supplier + Outlet-level Patient ID | Matched | |
| 3 | Match on Supplier + Outlet + Rx# | Matched | |
| 4 | Match on NCPDP ID + NCPDP Qualifier | Matched | How confident are we in the correctness of hits field? |
| 5 | DOB is non-match or missing | Not-Matched | A match on DOB is a must! |

TABLE 6-continued

Match Logic

| Level | Test | Record Matched/Not-Matched | Notes |
|---|---|---|---|
| 6 | Gender is a non-match | Not-Matched | Gender can be missing, but if populated, must match |
| 7 | DOB + (Insurance + All 5 Group A variables) | Matched | Matches on all demographic variables |
| 8 | DOB + (Insurance ID + Gender) | Matched | Accounts for 3rd party payers and can identify changes in address, first and last name |
| 9 | If Gender = Male and Last Name does not match | Not-Matched | We assume that a man's last name cannot change. If gender = M and last name missing then go to the next level. |
| 10 | 3 out of 5 variables in Group A do not match | Not-Matched | Does not matter which variables do not match |
| 11 | DOB + (4 out of 5 variables in Group A match) | Matched | Accounts for cash payers and changes in insurance numbers |
| 12 | DOB + (3 out of 5 variables in Group A match) | Possibly Matched | |
| 13 | Else | Not-Matched | |

| Demographic variables | Group A | Variables that can change |
|---|---|---|
| Insurance Card | Gender | Insurance Card - new plan |
| DOB | Patient Zip | Patient Zip - move |
| Gender | Last Name | Last Name - marry |
| Patient Zip | First Name | First Name - nickname, incorrect entry |
| Last Name | Address # | Address # - move |
| First Name | | |
| Address# | | |

TABLE 7

Match Logic
5C3 = DOB always
5 Set = (Gender, Zip Code, Last Name, First Name, Address)

| 10 combinations | | | | Example | Conflict | Conflict Likelihood | Left Out | | Does Missing vs. Non-Match Matter for Left Out Variables? | Match/Not Match |
|---|---|---|---|---|---|---|---|---|---|---|
| DOB | Gender | Zip | Last | Jun. 1, 1978, M, 12345, Smith | Multiple male Smiths with same DOB in same zip code | 6 - Medium | First | Address | No | ? |
| DOB | Gender | Zip | First | Jun. 1, 1978, M, 12345, John | Multiple Johns with same DOB within the same zip code | 7 - Medium High | Last | Address | Non-match Last name resolved in level 9 | Not-Match |
| DOB | Gender | Zip | Address | Jun. 1, 1978, M, 12345, #987 | Males with same DOB in same zip code | 9 - High | Last | First | Non-match Last name resolved in level 9 | Not-Match |
| DOB | Gender | Last | First | Jun. 1, 1978, M, Smith, John | John Smith with same DOB | 6 - Medium | Zip | Address | No | ? |
| DOB | Gender | Last | Address | Jun. 1, 1978, M. Smith, #987 | Multiple male Smiths with same DOB and same address numbers | 5 - Medium | Zip | First | No | ? |
| DOB | Gender | First | Address | Jun. 1, 1978, M, John, #987 | Multiple Johns with same DOB within the same address numbers | 6 - Medium | Zip | Last | Non-match Last name resolved in level 9 | ? |
| DOB | Zip | Last | First | Jun. 1, 1978, 12345, Smith, John | Multiple John Smiths with same DOB and zip code | 3 - Low | Gender | Address | Non-match gender resolved in level 6 | Match |
| DOB | Zip | Last | Address | Jun. 1, 1978, 12345, Smith, #987 | Multiple Smith with same DOB and address number | 5 - Medium | Gender | First | Non-match gender resolved in level 6 | ? |
| DOB | Zip | First | Address | Jun. 1, 1978, 12345, John, #987 | Multiple Johns with same DOB and address numbers | 6 - Medium | Gender | Last | Non-matches gender and last name resolved in steps 6 and 9 | ? |
| DOB | Last | First | Address | Jun. 1, 1978, Smith, John, #987 | Multiple John Smiths with same DOB and address # | 3 - Low | Gender | Zip | Non-Match gender resolved in level 6 | Match |

*Qualitatively assigned
1 = Low likelihood of conflict, or non-match;
5 = Medium likelihood of conflict;
10 = High likelihood of conflict.

Tables 8A-8E shows matching results for various combinations of data attributes under different scenarios in which the test data records included or excluded specific types of data attributes. Table 8A shows test results for test data records which included Insurance Card, DOB and Gender information. Table 8B shows test results for test data records which included Insurance Card and DOB information but lacked Gender information. Table 8C shows test results for test data records that included Insurance Card but lacked DOB information. Conversely, Table 8D shows test results for test data records, which included DOB information but lacked Insurance Card information. Table 8E shows test results for test data records that lacked both DOB information and Insurance Card information.

TABLE 8A

| Within Supplier | Count | Supplier ID | Insurance ID # | Patient DOB | Patient Gender | Patient Zip Code | Last Name | First Name | Address Numbers | Number Matched | Accepted? | Recom. |
|---|---|---|---|---|---|---|---|---|---|---|---|---|
| Has Insurance Card, DOB, and Gender | 1 | X | X | X | X | X | X | X | X | 8 | Y | |
| | 2 | X | X | X | X | X | X | X | O | 7 | Y | |
| | 3 | X | X | X | X | X | X | O | X | 7 | Y | |
| | 4 | X | X | X | X | X | O | X | X | 7 | Y | |
| | 5 | X | X | X | X | O | X | X | X | 7 | Y | |
| | 6 | X | X | X | X | X | X | O | O | 6 | Y | |
| | 7 | X | X | X | X | X | O | X | O | 6 | Y | |
| | 8 | X | X | X | X | O | O | X | X | 6 | Y | |
| | 9 | X | X | X | X | X | O | O | X | 6 | Y | |
| | 10 | X | X | X | X | O | X | O | X | 6 | Y | |
| | 11 | X | X | X | X | O | O | X | X | 6 | Y | |
| | 12 | X | X | X | X | X | O | O | O | 5 | Y | |
| | 13 | X | X | X | X | O | X | O | O | 5 | Y | |
| | 14 | X | X | X | X | O | O | X | O | 5 | Y | |
| | 15 | X | X | X | X | O | O | O | X | 5 | Y | |
| | 16 | X | X | X | X | O | O | O | O | 4 | Y | |

TABLE 8B

| Within Supplier | Count | Supplier ID | Insurance ID # | Patient DOB | Patient Gender | Patient Zip Code | Last Name | First Name | Address Numbers | Number Matched | Accepted? | Recom. |
|---|---|---|---|---|---|---|---|---|---|---|---|---|
| Has Insurance Card and DOB | 17 | X | X | X | O | X | X | X | X | 7 | ? | Y |
| | 18 | X | X | X | O | X | X | X | O | 6 | ? | Y |
| | 19 | X | X | X | O | X | X | O | X | 6 | ? | N |
| | 20 | X | X | X | O | X | O | X | X | 6 | ? | Y |
| | 21 | X | X | X | O | O | X | X | X | 6 | ? | Y |
| | 22 | X | X | X | O | X | X | O | O | 5 | ? | N |
| | 23 | X | X | X | O | X | O | X | O | 5 | ? | Y |
| | 24 | X | X | X | O | O | X | X | O | 5 | ? | Y |
| | 25 | X | X | X | O | X | O | O | X | 5 | ? | N |
| | 26 | X | X | X | O | O | O | X | X | 5 | ? | N |
| | 27 | X | X | X | O | O | O | X | X | 5 | ? | Y |
| | 28 | X | X | X | O | X | O | O | O | 4 | ? | N |
| | 29 | X | X | X | O | O | X | O | O | 4 | ? | N |
| | 30 | X | X | X | O | O | O | X | O | 4 | ? | Y |
| | 31 | X | X | X | O | O | O | O | O | 3 | ? | N |
| | 32 | X | X | X | O | O | O | O | O | 3 | ? | N |

TABLE 8C

| Within Supplier | Count | Supplier ID | Insurance ID # | Patient DOB | Patient Gender | Patient Zip Code | Last Name | First Name | Address Numbers | Number Matched | Accepted? | Rec. |
|---|---|---|---|---|---|---|---|---|---|---|---|---|
| Has Insurance Card, but missing DOB | 33 | X | X | O | X | X | X | X | X | 7 | ? | N |
| | 34 | X | X | O | X | X | X | X | O | 6 | ? | N |
| | 35 | X | X | O | X | X | X | O | X | 6 | ? | N |
| | 36 | X | X | O | X | X | X | O | O | 5 | ? | N |
| | 37 | X | X | O | X | X | O | X | X | 6 | ? | N |
| | 38 | X | X | O | X | X | O | O | O | 5 | ? | N |
| | 39 | X | X | O | X | X | O | O | O | 5 | ? | N |
| | 40 | X | X | O | X | X | O | O | O | 4 | ? | N |
| | 41 | X | X | O | X | O | X | X | X | 6 | ? | N |
| | 42 | X | X | O | X | O | X | X | O | 5 | ? | N |
| | 43 | X | X | O | X | O | X | O | X | 5 | ? | N |
| | 44 | X | X | X | X | X | O | O | O | 5 | ? | N |
| | 45 | X | X | O | X | O | O | X | X | 5 | ? | N |
| | 46 | X | X | O | X | O | O | X | O | 4 | ? | N |
| | 47 | X | X | O | X | O | O | O | X | 4 | ? | N |

TABLE 8C-continued

| Within Supplier | Count | Supplier ID | Insurance ID # | Patient DOB | Patient Gender | Patient Zip Code | Last Name | First Name | Address Numbers | Number Matched | Accepted? | Rec. |
|---|---|---|---|---|---|---|---|---|---|---|---|---|
| | 48 | X | X | O | X | O | O | O | O | 3 | ? | N |
| | 49 | X | X | O | O | X | X | X | X | 6 | ? | N |
| | 50 | X | X | O | O | X | X | X | O | 5 | ? | Y |
| | 51 | X | X | O | O | X | X | O | X | 5 | ? | N |
| | 52 | X | X | O | O | X | X | O | O | 4 | ? | N |
| | 53 | X | X | O | O | X | O | X | X | 5 | ? | N |
| | 54 | X | X | O | O | X | O | X | O | 4 | ? | N |
| | 55 | X | X | O | O | X | O | O | X | 4 | ? | N |
| | 56 | X | X | O | O | X | O | O | O | 3 | ? | N |
| | 57 | X | X | O | O | O | X | X | X | 5 | ? | N |
| | 58 | X | X | O | O | O | X | X | O | 4 | ? | N |
| | 59 | X | X | O | O | O | X | O | X | 4 | ? | Y |
| | 60 | X | X | O | O | O | X | O | O | 3 | ? | N |
| | 61 | X | X | O | O | O | O | X | X | 4 | ? | N |
| | 62 | X | X | O | O | O | O | X | O | 3 | ? | N |
| | 63 | X | X | O | O | O | O | O | X | 3 | ? | N |
| | 64 | X | X | O | O | O | O | O | O | 2 | ? | N |

TABLE 8D

| Within Supplier | Count | Supplier ID | Insurance ID # | Patient DOB | Patient Gender | Patient Zip Code | Last Name | First Name | Address Numbers | Number Matched | Accepted? | Recom. |
|---|---|---|---|---|---|---|---|---|---|---|---|---|
| Missing | 65 | X | O | X | X | X | X | X | X | 7 | ? | |
| Insurance | 66 | X | O | X | X | X | X | X | O | 6 | Y | |
| Card, | 67 | X | 0 | X | X | X | X | O | X | 6 | Y | |
| Has, | 68 | X | O | X | X | X | X | O | O | 5 | Y | |
| DOB | 69 | X | O | X | X | X | O | X | X | 6 | ? | N |
| | 70 | X | O | X | X | X | O | X | O | 5 | ? | N |
| | 71 | X | O | X | X | X | O | O | X | 5 | ? | N |
| | 72 | X | O | X | X | X | O | O | O | 4 | ? | N |
| | 73 | X | O | X | X | O | X | X | X | 6 | ? | N |
| | 74 | X | O | X | X | O | X | X | O | 5 | ? | N |
| | 75 | X | O | X | X | O | X | O | X | 5 | ? | N |
| | 76 | X | O | X | X | O | X | O | O | 4 | ? | N |
| | 77 | X | O | X | X | O | O | X | X | 5 | ? | N |
| | 78 | X | O | X | X | O | O | X | O | 4 | ? | X |
| | 79 | X | O | X | X | O | O | O | X | 4 | N | |
| | 80 | X | O | X | X | O | O | O | O | 3 | N | |
| | 81 | X | O | X | O | X | X | X | X | 6 | Y | |
| | 82 | X | O | X | O | X | X | X | O | 5 | ? | Y |
| | 83 | X | O | X | O | X | X | O | X | 5 | ? | Y |
| | 84 | X | O | X | O | X | X | O | O | 4 | ? | N |
| | 85 | X | O | X | O | X | O | X | X | 5 | ? | N |
| | 86 | X | O | X | O | X | O | X | O | 4 | ? | N |
| | 87 | X | O | X | O | X | O | O | X | 4 | ? | N |
| | 88 | X | O | X | O | X | O | O | O | 3 | N | |
| | 89 | X | O | X | O | O | X | X | X | 5 | ? | Y |
| | 90 | X | O | X | X | O | O | X | X | O | 4 | ? |
| | 91 | X | O | X | O | O | X | O | X | 4 | ? | N |
| | 92 | X | O | X | O | O | X | O | O | 3 | N | |
| | 93 | X | O | X | O | O | O | X | X | 4 | ? | N |
| | 94 | X | O | X | O | O | O | X | O | 3 | N | |
| | 95 | X | O | X | O | O | O | O | X | 3 | N | |
| | 96 | X | O | X | O | O | O | O | O | 2 | N | |

TABLE 8E

| Within Supplier | Count | Supplier ID | Insurance ID # | Patient DOB | Patient Gender | Patient Zip Code | Last Name | First Name | Address Numbers | Number Matched | Accepted? | Recom. |
|---|---|---|---|---|---|---|---|---|---|---|---|---|
| Missing | 97 | X | O | O | X | X | X | X | X | 6 | ? | N |
| Insurance | 98 | X | O | O | X | X | X | X | O | 5 | ? | N |
| Card | 99 | X | O | O | X | X | X | O | X | 5 | N | |
| AND | 100 | X | O | O | X | X | X | O | O | 4 | N | |
| DOB | 101 | X | O | O | X | X | O | X | X | 5 | N | |
| | 102 | X | O | O | X | X | O | X | O | 4 | N | |
| | 103 | X | O | O | X | X | O | O | X | 4 | N | |

TABLE 8E-continued

| Within Supplier | Count | Supplier ID | Insurance ID # | Patient DOB | Patient Gender | Patient Zip Code | Last Name | First Name | Address Numbers | Number Matched | Accepted? | Recom. |
|---|---|---|---|---|---|---|---|---|---|---|---|---|
| | 104 | X | O | O | X | X | O | O | O | O | 3 | |
| | 105 | X | O | O | X | O | X | X | X | 5 | ? | |
| | 106 | X | O | O | X | O | X | X | 0 | 4 | N | |
| | 107 | X | O | O | X | O | X | O | O | 3 | N | |
| | 108 | X | O | O | X | O | O | X | X | 4 | N | |
| | 109 | X | O | O | X | O | O | O | X | 3 | N | |
| | 110 | X | O | O | X | O | O | X | O | 3 | N | |
| | 111 | X | O | O | X | O | O | O | X | 3 | N | |
| | 112 | X | O | O | X | O | O | O | O | 2 | N | |
| | 113 | X | O | O | O | X | X | X | X | 5 | N | |
| | 114 | X | O | O | O | X | X | X | O | 4 | N | |
| | 115 | X | O | O | O | X | X | O | X | 4 | N | |
| | 116 | X | O | O | O | X | X | O | O | 3 | N | |
| | 117 | X | O | O | O | X | O | X | X | 4 | N | |
| | 118 | X | O | O | O | X | O | X | O | 3 | N | |
| | 119 | X | O | O | O | X | O | O | X | 3 | N | |
| | 120 | X | O | O | O | X | O | O | O | 2 | N | |
| | 121 | X | O | O | O | O | X | X | X | 4 | N | |
| | 122 | X | O | O | O | O | X | X | O | 3 | N | |
| | 123 | X | O | O | O | O | X | O | X | 3 | N | |
| | 124 | X | O | O | O | O | X | O | O | 2 | N | |
| | 125 | X | O | O | O | O | O | X | X | 3 | N | |
| | 126 | X | O | O | O | O | O | X | O | 2 | N | |
| | 127 | X | O | O | O | O | O | O | X | 2 | N | |
| | 128 | X | O | O | O | O | O | O | O | 1 | N | |
| | 129 | | | | | | | | | | | |

Analysis of test results such as shown in Tables 8A-8E provide an experimental basis for recommending or selecting particular sets of data attributes and levels for effective matching process implementations.

Further analysis or testing may be carried out to refine the matching logic for other data processing situations or circumstances. For example, for "across suppliers" matching processes a "store universe" data file may be analyzed to determine how often two data suppliers (e.g. McKesson and PDX) have stores in the same geographies. This analysis may help determine the patient travel match expectations between, for example, McKesson and PDX patients. The data attributes that may be considered in the analysis may, for example, include State, County, MSA, Zip Code 5-digit and Zip Code 3-digit It will be understood that the foregoing is only illustrative of the principles of the invention, and that various modifications can be made by those skilled in the art, without departing from the scope and spirit of the invention, which is limited only by the claims that follow.

I claim:

1. A method for assigning a longitudinal linking tag to a subject data record whose data attributes include at least some alphanumeric identification code attributes, third party attributes and demographic attributes related to the patient healthcare transaction, the method comprising the steps of:
    (a) defining a hierarchy of matching levels, wherein each matching level of said matching levels is defined by a designated set of data attributes for comparison with reference data records associated with known longitudinal linking tags, wherein the matching levels in the hierarchy are organized according to matching effectiveness of the data attributes within each respective matching level, and wherein the hierarchy of matching levels comprises a first series of matching levels, each matching level defined by a designated set of alphanumeric identification code attributes and a second series of matching levels, each matching level defined by a designated set of attributes including demographic attributes;
    (b) comparing values of the designated sets of data attributes in the subject data record and the reference data records level by level through the first series of matching levels in an attempt to find a matching reference data record;
    (c) if no matching reference data record is found at step (b), determining, by a computer processor, that at least a relevant demographic attribute is present in the subject data record;
    (d) if at least the relevant demographic attribute is present in the subject data record, comparing values of the designated sets of data attributes in the subject data record and the reference data records level by level through the second series of matching levels in an attempt to find a matching reference data record;
    (e) if a matching reference data record is found, assigning the longitudinal linking tag associated with that reference data record to the subject data record;
    (f) generating a new longitudinal linking tag and assigning the new longitudinal linking tag to the subject data record when no reference data records are successfully matched to the subject data record at steps (b) through (e); and
    (g) comparing values of demographic attributes in the subject data record and the matching reference data record found at step (b) to confirm the matching of the two records,
    wherein the matching levels are arranged in an hierarchical sequence according to empirically determined matching effectiveness ranks of the designated sets of data attributes defining each match level.

2. The method of claim 1, wherein at least a matching level in the first series of matching levels is defined by a set of attributes selected from a group of Supplier Patient ID, Supplier ID, Outlet ID, Rx No., NCPDP Qualifier, NCPDP ID attributes and any combination thereof.

3. The method of claim 1, wherein in step (c) the relevant attribute is the DOB attribute.

4. The method of claim 1, wherein at least a matching level in the second series of matching levels is defined by a set of demographic attributes selected from a group of Insurance Card No., DOB, Gender, Patient Zip Code, Last Name, First Name, Address No., and any combination thereof.

5. The method of claim 1 wherein step (g) comprises comparing the values of DOB and Gender attributes in the subject data record and the matching reference data record to confirm the matching of the two records.

6. The method of claim 1 wherein step (g) comprises comparing values of Last Name and Zip Code attributes in the subject data record and the matching reference data record to confirm the matching of the two records.

7. A computer readable storage medium having instructions that are executed by a computer for performing steps of:
assigning a longitudinal linking tag to a subject data record whose data attributes include at least some alphanumeric identification code attributes, third party attributes and demographic attributes related to the patient healthcare transaction;
(a) defining a hierarchy of matching levels, wherein each matching level of said matching levels is defined by a designated set of data attributes for comparison with reference data records associated with known longitudinal linking tags, wherein the matching levels in the hierarchy are organized according to matching effectiveness of the data attributes within each respective matching level, and wherein the hierarchy of matching levels comprises a first series of matching levels, each matching level defined by a designated set of alphanumeric identification code attributes and a second series of matching levels, each matching level defined by a designated set of attributes including demograhic attributes;
(b) comparing values of the designated sets of data attributes in the subject data record and the reference data records level by level through the first series of matching levels in an attempt to find a matching reference data record;
(c) if no matching reference data record is found at step (b), determining, by a computer processor, that at least a relevant demographic attribute is present in the subject data record;
(d) if at least the relevant demographic attribute is present in the subject data record, comparing values of the designated sets of data attributes in the subject data record and the reference data records level by level through the second series of matching levels in an attempt to find a matching reference data record;
(e) if a matching reference data record is found, assigning the longitudinal linking tag associated with that reference data record to the subject data record;
(f) generating a new longitudinal linking tag and assigning the new longitudinal linking tag to the subject data record when no reference data records are successfully matched to the subject data record at steps (b) through (e); and
(g) comparing values of demographic attributes in the subject data record and the matching reference data record found at step (b) to confirm the matching of the two records,
wherein the matching levels are arranged in an hierarchical sequence according to empirically determined matching effectiveness ranks of the designated sets of data attributes defining each match level.

8. A longitudinal database including at least one subject data record with an assigned longitudinal linking tag encoded on a computer readable storage medium, wherein the at least one subject data record includes at least some alphanumeric identification code attributes, third party attributes and demographic attributes, the longitudinal database created using a procedure comprising:
(a) defining a hierarchy of matching levels, wherein each matching level of said matching levels is defined by a designated set of data attributes for comparison with reference data records associated with known longitudinal linking tags, wherein the matching levels in the hierarchy are organized according to matching effectiveness of the data attributes within each respective matching level, and wherein the hierarchy of matching levels comprises a first series of matching levels, each matching level defined by a designated set of alphanumeric identification code attributes and a second series of matching levels, each matching level defined by a designated set of attributes including demographic attributes;
(b) comparing values of the designated sets of data attributes in the at least one subject data record and the reference data records level by level through the first series of matching levels in an attempt to find a matching reference data record;
(c) if no matching reference data record is found at step (b), determining, by a computer processor, that at least a relevant demographic attribute is present in the at least one subject data record;
(d) if at least the relevant demographic attribute is present in the at least one subject data record, comparing values of the designated sets of data attributes in the at least one subject data record and the reference data records level by level through the second series of matching levels in an attempt to find a matching reference data record;
(e) if a matching reference data record is found, assigning the longitudinal linking tag associated with that reference data record to the at least one subject data record;
(f) generating a new longitudinal linking tag and assigning the new longitudinal linking tag to the at least one subject data record when no reference data records are successfully matched to the at least one subject data record at steps (b) through (e); and
(g) comparing values of demographic attributes in the at least one subject data record and the matching reference data record found at step (b) to confirm the matching of the two records,
wherein the matching levels are arranged in an hierarchical sequence according to empirically determined matching effectiveness ranks of the designated sets of data attributes defining each match level.

9. The longitudinal database of claim 8 wherein the at least one subject data record is successfully matched to a reference data record only at a level in the second series of matching levels upon comparison of a designated set of demographic attributes and is assigned the longitudinal linking tag associated with the successfully matched reference data record.

* * * * *